US008242165B2

(12) United States Patent
Dash et al.

(10) Patent No.: US 8,242,165 B2
(45) Date of Patent: Aug. 14, 2012

(54) MUCOADHESIVE NANOPARTICLES FOR CANCER TREATMENT

(75) Inventors: Alekha K. Dash, Omaha, NE (US); William J. Trickler, Omaha, NE (US)

(73) Assignee: Creighton University, Omaha, NE (US)

( * ) Notice: Subject to any disclaimer, the term of this patent is extended or adjusted under 35 U.S.C. 154(b) by 177 days.

(21) Appl. No.: 12/311,479

(22) PCT Filed: Oct. 26, 2007

(86) PCT No.: PCT/US2007/022702
§ 371 (c)(1),
(2), (4) Date: Mar. 31, 2009

(87) PCT Pub. No.: WO2008/105852
PCT Pub. Date: Sep. 4, 2008

(65) Prior Publication Data
US 2010/0323977 A9    Dec. 23, 2010

Related U.S. Application Data

(60) Provisional application No. 60/854,577, filed on Oct. 26, 2006.

(51) Int. Cl.
*A61K 31/335* (2006.01)
*A61K 47/00* (2006.01)
*A61K 31/70* (2006.01)

(52) U.S. Cl. .......................... 514/449; 514/27; 514/777

(58) Field of Classification Search .................. 514/449, 514/27, 777
See application file for complete search history.

(56) References Cited

U.S. PATENT DOCUMENTS

| | | | |
|---|---|---|---|
| 4,534,899 A | 8/1985 | Sears | |
| 5,248,796 A | 9/1993 | Chen et al. | |
| 5,504,102 A | 4/1996 | Agharkar et al. | |
| 5,670,537 A | 9/1997 | Caretta et al. | |
| 6,030,818 A | 2/2000 | Page et al. | |
| 6,096,331 A * | 8/2000 | Desai et al. | 424/422 |
| 6,184,037 B1 | 2/2001 | Rolland et al. | |
| 6,716,627 B2 | 4/2004 | Doble | |
| 6,979,456 B1 | 12/2005 | Parikh et al. | |
| 2004/0219214 A1 | 11/2004 | Gravett et al. | |
| 2004/0220081 A1 * | 11/2004 | Kreitz et al. | 514/2 |
| 2006/0013885 A1 | 1/2006 | Nah et al. | |

OTHER PUBLICATIONS

Ganguly et al. (International J. of Pharmaceutics 27691-2) 2004, 83-92).*
Manthena et al. (Eur. J. Pharm Sci (2005) 25(4-5):445-453.*
Jauhari et al. (AAPS PharmaSciTech (2006), 7(2), E1 -E6).*
Prabha et al., Nanoparticle-Mediated Wild-Type p53 Gene Delivery Results in Sustained Antiproliferative Activity in Breast Cancer Cells, Molecular Pharmaceutics, 2004, vol. 1, iss. 3, pp. 211-219.
Ajani, et al., Phase II Study of Taxol in Patients with Advanced Gastric Carcinoma, Cancer J. Sci. Am., 1998, vol. 4, iss. 4, pp. 269-274.
Chao et al., Paclitaxel in a Novel Formulation Containing less Cremophor EL as First-Line Therapy for Advanced Breast Cancer: A Phase II Trial, Invest. New Drugs, 2005, vol. 23, iss. 2, pp. 171-177.
Gelderblom et al., Cremophor EL: the drawbacks and advantages of vehicle selection for drug formulation, Eur. J. Cancer, 2001, vol. 37, iss. 13, pp. 1590-1598.
Singla et al., Paclitaxel and Its Formulations, Int. J. Pharm., 2002, vol. 235, iss. 1-2, pp. 179-192.
Rowinsky et al., Neurotoxicity of Taxol, J. Natl. Cancer Inst. Monogr., 1993, iss. 15, pp. 107-115.
Ibrahim et al., Phase I and Pharmacokinetic Study of ABI-007, a Cremophor-Free Protein-Stabilized, Nanoparticle Formulation of Paclitaxel, Clin. Cancer Res., 2002, vol. 8, iss. 5, pp. 1038-1044.
Gradishar, Albumin-Bound Paclitaxel: A Next-Generation Taxane, Expert Opin. Pharmacother., 2006, vol. 7, iss. 8, pp. 1041-1053.
Socinski, Update on Nanoparticle Albumin-Bound Paclitaxel, Clin. Adv. Hematol. Oncol., 2006, vol. 4, iss. 10, pp. 745-746.
Chhieng et al., MUC1 and MUC2 Expression in Pancreatic Ductal Carcinoma Obtained by Fine-Needle Aspiration, Cancer, 2003, vol. 99, iss. 6, pp. 365-371.
Sternberg et al., Alternative splicing of the Human MUC2 gene, Arch. Biochem Biophys, 2004, vol. 421, iss. 1, pp. 21-33.
Magro et al., Differential expression of Mucins 1-6 in Papillary Thyroid Carcinoma: Evidence for Transformation-Dependent Post-Translational Modification of MUC1 In Situ, J. Path., 2003, vol. 200, iss. 3, pp. 357-369.
Feng et al., Expression of MUC1 and MUC2 Mucin Gene Products in Human Ovarian Carcinomas, 2002, Jpn. J. Clin. Oncol. vol. 32, iss. 12, pp. 525-529.
Berger et al., Respiratory Carcinoma Cell Lines. MUC Genes and Glycoconjugates, Am. J. Respir. Cell Mol. Biol., 1999, vol. 20, iss. 3, pp. 500-510.
Panyam et al., Targeting intracellular targets, Curr. Drug Deliv., 2004, vol. 1, iss. 3, pp. 235-247.
Dash et al., X-Ray Powder Diffractometric Method for Quantitation of Crystalline Drug in Microparticulate Systems. I. Microspheres, J. Pharm. Sci, 2002, vol. 91, iss. 4, pp. 983-990.
De Campos et al., Chitosan Nanoparticles: A New Vehicle for the Improvement of the Delivery of Drugs to the Ocular Surface. Application to Cyclosporin A, Int. J. Pharm, 2001, vol. 224, iss. 1-2, pp. 159-168.
Wu et al., Chitosan Nanoparticles as a Novel Delivery System for Ammonium Glycyrrhizinate, Int. J. Pharm., 2005, vol. 295, iss.1 -2, pp. 235-245.

(Continued)

*Primary Examiner* — Brandon Fetterolf
*Assistant Examiner* — Shirley V Gembeh
(74) *Attorney, Agent, or Firm* — Valauskas Corder LLC

(57) ABSTRACT

The present invention relates to a pharmaceutical composition which includes nanoparticles. The nanoparticles include a glyceryl monooleate or monolinoleate (or other mono fatty acid ester); a chitosan; and a cancer therapeutic agent, such as gemcitabine, taxanes, and hydrophobic cancer therapeutic agents). Also disclosed are methods for preparing such nanoparticles and pharmaceutical compositions, as well as methods for treating breast, pancreatic, colon, prostate, and other cancers by parenterally, intravenously, or otherwise administering such nanoparticles and pharmaceutical compositions.

14 Claims, 9 Drawing Sheets

OTHER PUBLICATIONS

Jeong et al., Polyion Complex Micelles Composed of All-Trans Retinoic Acid and Poly (Ethylene Glycol)—Grafted Chitosan, J. Pharm. Sci., 2006, vol. 95, iss. 11, pp. 2348-2360.

Hu et al., Shell Cross-Linked Stearic Acid Grafted Chitosan Oliosaccharide Self-Aggregated Micelles for Controlled Release of Paclitaxel, Colloids Surf. B Bioninterfaces, 2006, vol. 50, iss. 2, pp. 97-103.

Kim et al., Hydrophobically Modified Glycol Chitosan Nanoparticles as Carriers for Paclitaxel, J. Control Release, 2006, vol. 111, iss. 1-2, pp. 228-234.

Maestrelli et al., A New Drug Nanocarrier Consisting of Chitosan and Hydoxypropylcyclodextrin, Eur J Pharm. Biopharm., 2006, vol. 63, iss. 2, pp. 79-86.

Agnihotri et al., Recent Advances on Chitosan-Based Micro- and Nanoparticles in Drug Delivery, J. Control. Release, 2004, vol. 100, iss. 1, pp. 5-28.

Prego et al., Chitosan-PEG Nanocapusules as New Carriers for Oral Peptide Delivery. Effect of Chitosan Pegylation Degree, J. Control. Release, 2006, vol. 111, iss. 3, pp. 299-308.

Garcia-Fuentes et al., A Comparative Study of the Potential of Solid Triglyceride Nanostructures Coated with Chitosan or Poly(Ethylene Glycol) as Carriers for Oral Calcitonin Delivery, Eur. J. Pharm. Sci, 2005, vol. 25, iss. 1, pp. 133-143.

Garg et al., Cubosomes: an Overview, Biol. Pharm. Bull., 2007, vol. 30, iss. 2, pp. 350-353.

Ganguly et al., A Novel in situ Gel for Sustained Drug Delivery and Targeting, Int. J. Pharm., 2004, vol. 276, iss. 1-2, pp. 83-92.

Sadhale et al., Glyceryl Monooleate Cubic Phase Gel as Chemical Stability Enhancer of Cefazolin and Cefuroxime, Pharm. Dev. Technol., 1998, vol. 3, iss. 4, pp. 549-556.

Uner, Preparation, Characterization and Physico-Chemical Properties of Solid Lipid Nanoparticles (SLN) and Nanostructured Lipid Carriers (NLC): Their Benefits as Colloidal Drug Carrier Systems, Pharmazie, 2006, vol. 61, iss. 5, pp. 375-386.

Bummer, Physcial Chemical Considerations of Lipid-Based Oral Drug Delivery—Solid Lipid Nanoparticles, Crit. Rev. Ther. Drug Carrier Syst., 2004, vol. 21, iss. 1, pp. 1-20.

Lockman et al., Nanoparticle Technology for Drug Delivery Across the Blood-Brain Barrier, Drug Dev. Ind. Pharm., 2002, vol. 28, iss. 1, pp. 1-13.

Douglas et al., Nanoparticles in Drug Delivery, Crit. Rev. Ther. Drug Carrier Syst., 1987, vol. 3, iss. 3, pp. 233-261.

Takeuchi et al., Mucoadhesive Nanoparticulate Systems for Peptide Drug Delivery, Adv. Drug Deliv. Rev., 2001, vol. 47, iss. 1, pp. 39-54.

Rogers, Taxol: A Promising New Drug of the 90s, Oncol. Nurs. Forum, 1993, vol. 20, iss. 10, pp. 1483-1489.

Tarr, et al., A New Parenteral Vehicle for the Administration of Some Poorly Soluble Anti-Cancer Drugs, J. Pareneter. Sci. Technol., 1987, vol. 41, pp. 31-33.

Friedland et al., Hypersensitivity Reactions from Taxol and Etopside, J. Natl. Cancer Inst., 1993, vol. 85, iss. 24, p. 2036.

J. Lee Villano, Abraxane Induced Life-Threatening Toxicities with Metastatic Breast Cancer and Hepatic Insufficiency, Invest. New Drugs, 2006, vol. 24, iss. 5, pp. 455-456.

Lutton, Phase Behavior of Aqueous Systems of Monoglycerides, J. Am. Oil Chem. Soc., 1965, vol. 42, iss. 12, pp. 1068-1070.

Sandri et al., Nanoparticles Based on N-Trimethylchitosan: Evaluation of Absorption Properties Using in vitro (Caco-2 Cells) and ex vivo (Excised Rat Jejunum) Models, Eur. J. Pharm. Biopharm., 2007, vol. 65, iss. 1, pp. 68-77.

Howard et al., RNA Interference In Vitro and In Vivo Using a Novel Chitosan/siRNA Nanoparticle System, Mol. Ther., 2006, vol. 14, iss. 4, pp. 476-484.

Shikata et al., In Vitro Cellular Accumulation of Gadolinium Incorporated into Chitosan Nanoparticles Designed for Neutron-Capture Therapy of Cancer, Eur. J. Pharm. Biopharm., 2002, vol. 53, iss. 1, pp. 57-63.

Wani et al., Plant Antitumor Agents, VI: The Isolation and Structure of Paclitaxe, a Novel Antileukemic and Antitumor Agent from Taxus Brevifolia, J. Am. Chem. Soc., 1971, vol., 93, pp. 2325-2327.

Essayan et al., Successful Parenteral Desensitization to Paclitaxel, J. Allergy and Clin. Immun., 1996, vol. 97, pp. 42-46.

Suffness, Taxol: From Discovery to Therapeutic Use, Annual Reports Med. Chem., 1993, vol. 28, pp. 305-314.

Riondel et al., Effects of Free and Liposome-With Encapsulated Taxol on Two Brain Tumors Xenografed into Nude Mice, In Vivo, 1992, vol. 6, pp. 23-28.

Einzig, et al., Phase II of Taxol in Patients with Metastatic Renal Cell Carcinoma, Cancer Investigation,1991, vol. 9, pp. 133-136.

Bartoli et al., In Vitro and In Vivo Antitumoral Activity and Free and Encapsulated Taxol, J. Microencapsulation, 1990, vol. 7, iss. 2, pp. 191-197.

Miller et al., Reporting Results of Cancer Treatment, Cancer, 1981, vol. 47, pp. 207-214.

Suffness, M., Taxol: Science and Applications, 1995, Boca Raton, Florida: CAC Press LLC.

* cited by examiner

MUCOADHESIVE NANOPARTICLES FOR CANCER TREATMENT

This application claims priority from PCT/US2007/022702, filed 26 Oct. 2007, which claims priority from U.S. Application Ser. No. 60/854,577 filed 26 Oct., 2006.

The present invention was made with the support of the Department of Defense's Concept Award No. BC045664. The Federal Government may have certain rights in this invention.

FIELD OF THE INVENTION

The subject invention is directed generally to methods and compositions for treating cancer and, more particularly, to a nanoparticulate delivery system for delivering taxanes and other drugs to subjects suffering from cancer.

BACKGROUND OF THE INVENTION

The localized or targeted delivery of chemotherapeutics has been exploited in recent trends to limit the indiscriminate toxicities to normal tissues associated with chemotherapy. In general, these toxicities are often the dose limiting factors in reaching effective therapeutics in cancerous tissues because they are often life threatening.

Paclitaxel ("PTX"), the first of a new class of microtubule stabilizing agents, is recognized as an effective chemotherapeutic for a wide variety of solid tumors (Ajani et al., "Phase II Study of Taxol in Patients with Advanced Gastric Carcinoma," Cancer J. Sci. Am., 4(4), 269-274 (1998); and Rogers, "Taxol: A Promising New Drug of the '90s," Oncol. Nurs. Forum, 20(10), 1483-1489 (1993), which are hereby incorporated by reference). Clinical application of this highly effective drug in the treatment of cancer is limited because of its poor aqueous solubility (0.6 mM) and poor oral bioavailability (Matthew Suffness, ed., Taxol: Science and Applications, Boca Raton, Fla.: CAC Press LLC (1995), which is hereby incorporated by reference). To date, only two commercial formulations have been developed. The first formulation developed uses 1:1 mixture of Cremophor EL and ethanol to increase the solubility of paclitaxel (7 mM) administered intravenously (Tarr et al., "A New Parenteral Vehicle for the Administration of Some Poorly Soluble Anti-Cancer Drugs," J. Parenteri. Technol., 41:31-33 (1987), which is hereby incorporated by reference). Cremophor may have serious adverse side effects including severe hypersensitivity reactions, neurotoxicity, nephrotoxicity, and hypotensive vasodilation (Chao et al., "Paclitaxel in a Novel Formulation Containing less Cremophor EL as First-Line Therapy for Advanced Breast Cancer: A Phase II Trial," Invest. New Drugs, 23(2):171-177 (2005); Gelderblom et al., "Cremophor EL: the drawbacks and advantages of vehicle selection for drug formulation," Eur. J. Cancer, 37(13):1590-1598 (2001); and Friedland et al., "Hypersensitivity Reactions from Taxol and Etoposide," J. Natl. Cancer Inst., 85(24):2036 (1993) ("Friedland"), which are hereby incorporated by reference). In addition to solvent-associated toxicity, paclitaxel has many indiscriminate side effects that can be life threatening. These include nausea, vomiting, hypersensitivity, bone marrow depression, and arrhythmias (Friedland; Singla et al., "Paclitaxel and Its Formulations," Int. J. Pharm., 235(1-2):179-192 (2002); and Rowinsky et al., "Neurotoxicity of Taxol," J. Natl. Cancer Inst. Monogr. (15):107-115 (1993), which are hereby incorporated by reference). The newest addition to the commercial marketplace, ABRAXANE™., is an injectable suspension of albumin-bound paclitaxel nanoparticles (Ibrahim et al., "Phase I and Pharmacokinetic Study of ABI-007, a Cremophor-Free, Protein-Stabilized, Nanoparticle Formulation of Paclitaxel," Clin. Cancer Res., 8(5):1038-1044 (2002); and Gradishar, "Albumin-Bound Paclitaxel: A Next-Generation Taxane," Expert Opin. Pharmacother., 7(8):1041-1053 (2006), which are hereby incorporated by reference). However, bone marrow suppression is not only the dose dependant and dose limiting toxicity, but also neuropathy toxicity has been shown to be remarkably increased when compared to the traditional PTX formulation (Socinski, "Update on Nanoparticle Albumin-Bound Paclitaxel," Clin. Adv. Hematol. Oncol., 4(10):745-746 (2006); and Lee Villano, J. et al., "Abraxane Induced Life-Threatening Toxicities with Metastatic Breast Cancer and Hepatic Insufficiency," Invest. New Drugs, 24(5):455-456 (2006), which are hereby incorporated by reference).

Poor aqueous solubility has also limited the usefulness of other chemotherapeutic agents.

In view of the above, a need continues to exist for formulations for the delivery of paclitaxel, other taxanes, and other chemotherapeutic agents, and the present invention is directed, in part, to addressing this need.

SUMMARY OF THE INVENTION

The present invention relates to a pharmaceutical composition which includes nanoparticles. The nanoparticles include a glyceryl mono fatty acid ester; a chitosan; and a cancer therapeutic agent.

BRIEF DESCRIPTION OF THE DRAWINGS

(FIG. 1a) and 50,000×. (FIG. 1b) showing the morphology and microstructure of chitosan/GMO nanoparticles according to the present invention.

DETAILED DESCRIPTION OF THE INVENTION

Figure 1A:
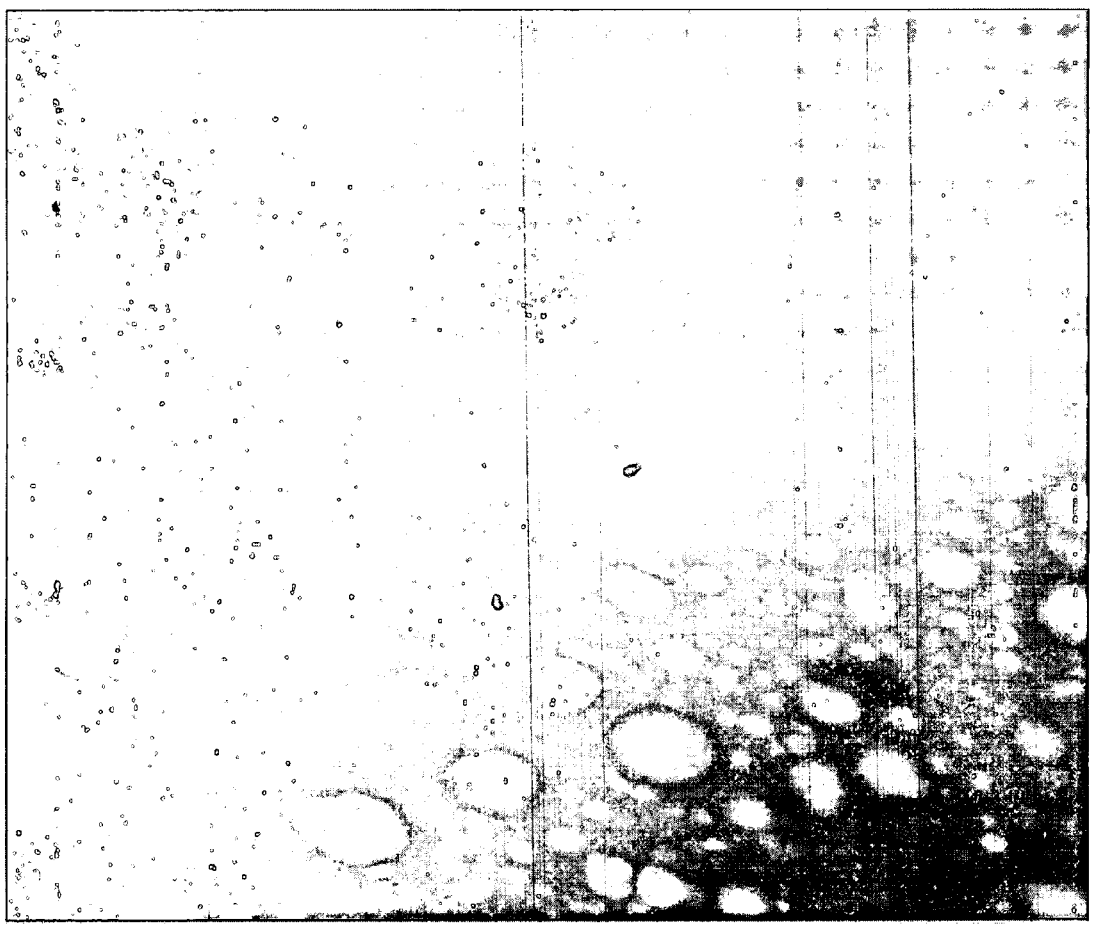
FIGS. 1A and 1B are transmission electron microscopy ("TEM") images of osmium tetroxide loaded chitosan/GMO nanoparticles at magnification 10,000×.

The present invention relates to a pharmaceutical composition which includes nanoparticles. The nanoparticles include a glyceryl mono fatty acid ester; a chitosan; and a cancer therapeutic agent.

"Nanoparticles", as used herein are meant to refer to a collection of particles, a substantial portion of which have diameters of less than about 5000 nm, such as less than about 4000 nm, less than about 3000 nm, less than about 2000 nm, from about 10 nm to about 2000 nm, from about 20 nm to about 2000 nm, from about 50 nm to about 2000 nm, from about 100 nm to about 2000 nm, from about 200 nm to about 2000 nm, from about 250 nm to about 2000 nm, from about 300 nm to about 2000 nm, from about 350 nm to about 2000 nm, from about 400 nm to about 2000 nm, from about 10 nm to about 1000 nm, from about 20 nm to about 1000 nm, from about 50 nm to about 1000 nm, from about 100 nm to about 1000 nm, from about 200 nm to about 1000 nm, from about 250 nm to about 1000 nm, from about 300 nm to about 1000 nm, from about 350 nm to about 1000 nm, from about 400 nm to about 1000 nm, less than 5000 nm, less than 4000 nm, less than 3000 nm, less than 2000 nm, from 10 nm to 2000 nm, from 20 nm to 2000 nm, from 50 nm to 2000 nm, from 100 nm to 2000 nm, from 200 nm to 2000 nm, from 250 nm to 2000 nm, from 300 nm to 2000 nm, from 350 nm to 2000 nm, from 400 nm to 2000 nm, from 10 nm to 1000 nm, from 20 nm to 1000 nm, from 50 nm to 1000 nm, from 100 nm to 1000 nm, from 200 nm to 1000 nm, from 250 nm to 1000 nm, from 300 nm to 1000 nm, from 350 nm to 1000 nm, from 400 nm to 1000 nm, etc. The shapes of the particles are not particularly critical: spherical particles are typical. Where non-spherical nanoparticles are employed, "diameter" is meant to refer to the diameter of a hypothetical sphere having the same volume of the non-spherical nanoparticle. For the purposes of the present invention, "a substantial portion" of the nanoparticles are to be deemed to have a specified diameter or a specified range of diameters when more than 50% (e.g., more than 60%, more than 65%, more than 70%, more than 75%, more than 80%, more than 85%, more than 90%, etc.) have diameters of the specified diameter or within the specified range of diameters.

"About", as used herein, is meant to include plus/minus 30%, such as plus/minus 25%, plus/minus 20%, plus/minus 15%, plus/minus 10%, plus/minus 5%, and/or plus/minus 0% (to within the uncertainty of measurement methods).

"Glyceryl mono fatty acid", as used herein, is meant to refer to the ester produced by reaction of a single glycerol molecule with a single fatty acid. Examples of fatty acids. The fatty acids can be saturated or unsaturated. Examples of saturated fatty acids include branched or unbranched saturated fatty acids, such as branched or unbranched C8 to C22 saturated fatty acids (e.g., caprylic acid (C8), capric acid (C10), lauric acid (C12), myristic acid (C14), palmitic acid (C16), stearic acid (C18), arachidic acid (C20), and behenic acid (C22)). Examples of unsaturated fatty acids include branched or unbranched mono-, di-, or tri-unsaturated fatty acids, such as branched or unbranched mono-, di-, or tri-unsaturated fatty acids, examples of which include branched or unbranched mono-, di-, or tri-unsaturated C14 to C22 fatty acids. Examples of unsaturated fatty acids also include omega-3 fatty acids, omega-5 fatty acids, omega-6 fatty acids, omega-7 fatty acids, omega-9 fatty acids. Still further examples of unsaturated fatty acids include myristoleic acid, palmitoleic acid, oleic acid, linoleic acid, alphalinoleic acid, arachidonic acid, eicosapentaeonic acid, erucic acid, and docosahexaenoic acid. The unsaturated fatty acids can be in the cis- or trans-configurations or mixtures of the two. In one embodiment the glyceryl mono fatty acid ester is selected from glyceryl monolaurate, glyceryl monopalmitate, glyceryl monostearate, glyceryl monolinoleate, glyceryl monooleate, oleyl glycerate and combinations thereof. In another embodiment the glyceryl mono fatty acid ester is selected from glyceryl monolinoleate, glyceryl monooleate, oleyl glycerate and combinations thereof. In another embodiment the glyceryl mono fatty acid ester is glyceryl monooleate. In another embodiment, the glyceryl mono fatty acid ester is oleyl glycerate.

"Chitosan", as used herein, is meant to refer to N-deacetylated chitin and other water-soluble derivatives of chitin.

"Cancer therapeutic agent", as used herein is meant to refer to drugs and other compounds that are useful in treating cancer. Examples of suitable cancer therapeutic agents include antineoplastics, such as adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, Taxol and derivatives thereof, taxotere and derivatives thereof, vinblastine, vincristine, tamoxifen, etoposide, piposulfan, and the like.

In certain embodiments, the cancer therapeutic agent is a gemcitabine.

In certain embodiments, the cancer therapeutic agent is a taxane. As used herein, "taxane" is meant to refer to a member of the family of compounds known as taxanes. "Taxane", as used herein, is meant to include paclitaxel, baccatin III, cephalomannine, 10-deacetylbaccatin III, 10-deacetyl-7-xylosyl paclitaxel C, 10-deacetyl paclitaxel, 10-deacetyl-7-xylosyl paclitaxel, 7-xylosyl paclitaxel, 7-epi paclitaxel, 10-deacetyl-7-epi paclitaxel, taxchins (e.g., taxcin A), taxchinins (e.g., taxchinin D, taxchinin E, taxchinin G, taxchinin H, taxchinin I, taxchinin J, taxchinin K, etc.), docetaxel, compounds having the following formulae:

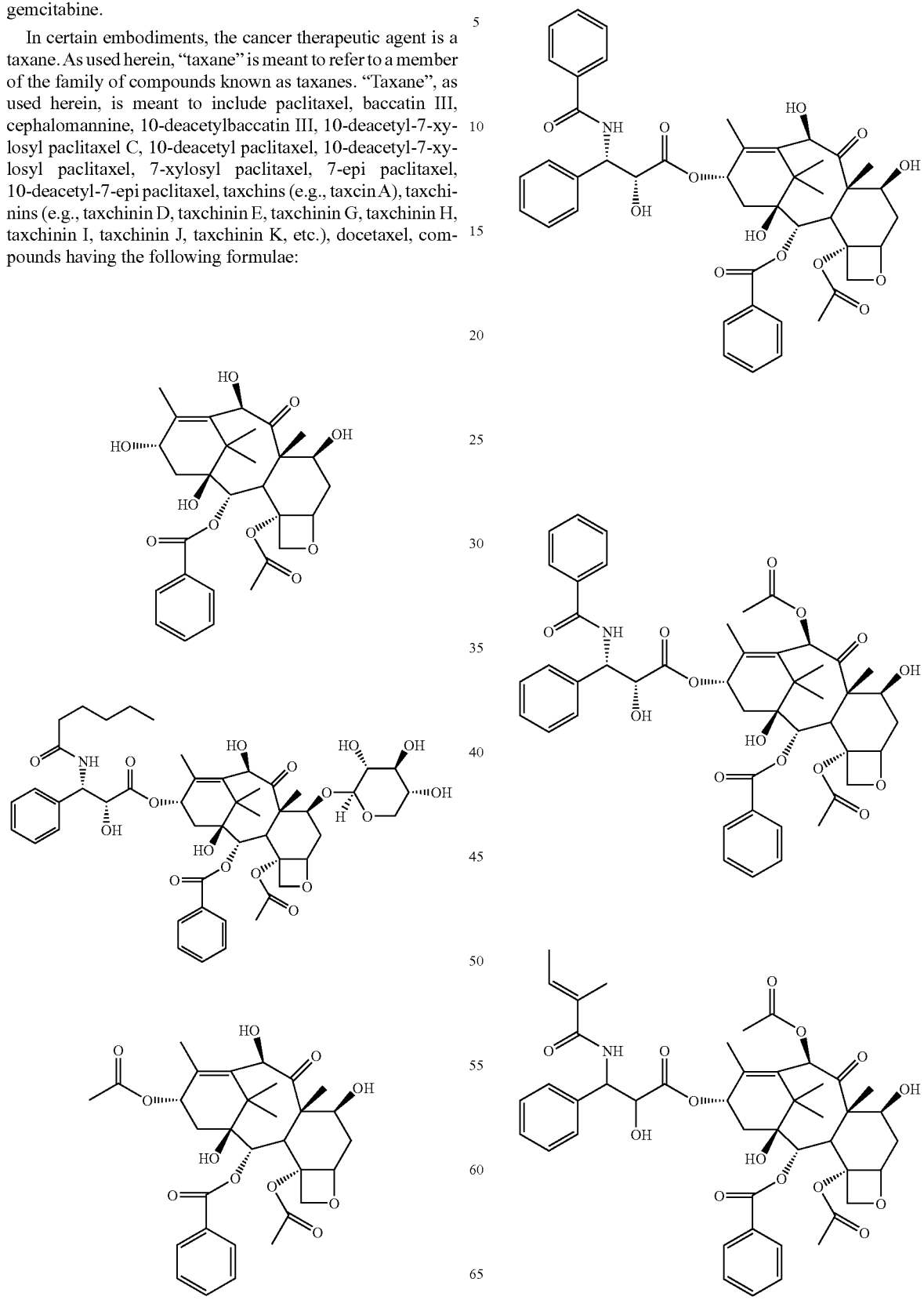

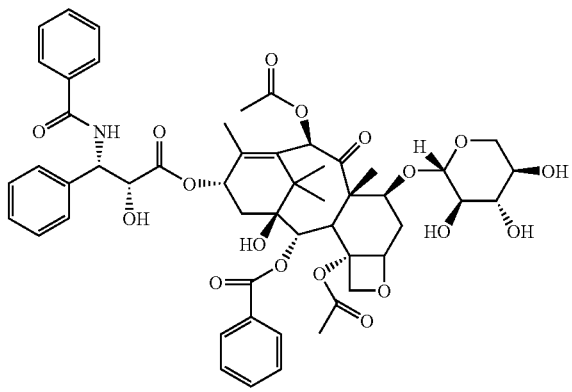

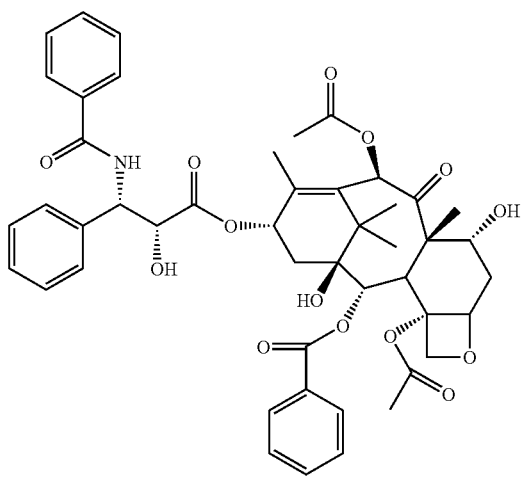

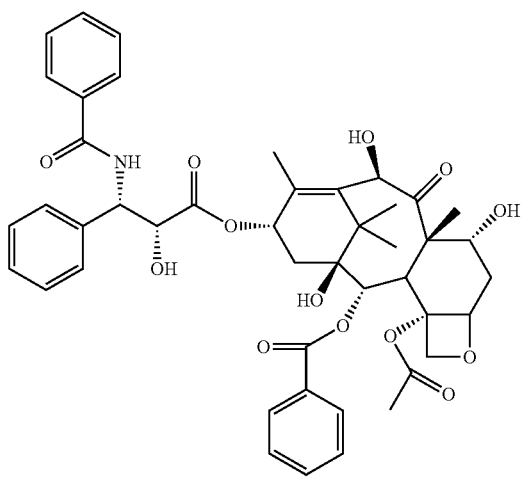

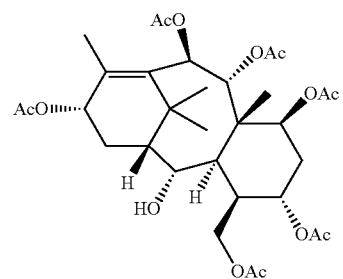

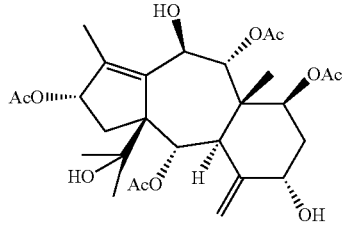

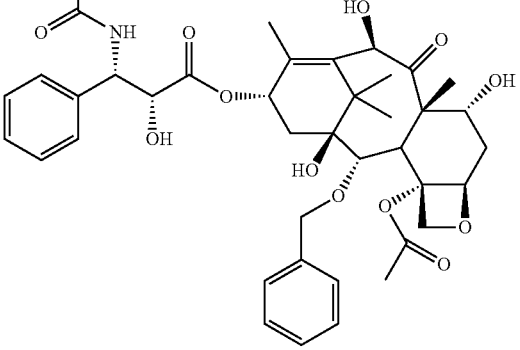

and other derivatives and compounds bearing the taxane core ring structure common to the aforementioned compounds. It is to be understood that a combination of the aforementioned compounds and/or other taxanes can be used in the practice of the present invention, and that "a taxane", as used herein, is meant to include such combinations. Moreover, it will be appreciated by the skilled reader that the taxanes may be capable of forming salts; and "taxane", as used herein, is meant to include pharmaceutically acceptable salt forms of the aforementioned taxanes and other taxanes. It should be recognized that the particular counterion forming a part of any pharmaceutically acceptable salt of this invention is usually not of a critical nature, so long as the salt as a whole is pharmacologically acceptable and as long as the counterion does not contribute undesired qualities to the salt as a whole. In addition, it will be appreciated by the skilled reader that the taxanes of the present invention may be capable of forming solvates, such as ethanol solvates, hydrates, and the like; and "taxane", as used herein, is meant to include such ethanol solvates, hydrates, and other solvates.

In certain embodiments, the cancer therapeutic agent is hydrophobic. In this context, a cancer therapeutic agent is to be considered to be hydrophobic either (A) when its solubility in water at room temperature is equal to or less than ten times (e.g., equal to or less than eight times, equal to or less than six times, equal to or less than five times, equal to or less than four times, equal to or less than thrice, equal to or less than twice, and/or equal to or less than) the solubility of paclitaxel in water at room temperature; and/or (B) when its solubility in water at room temperature is less than or equal to about 6 mM, such as less than or equal to about 5 mM, less than or equal to about 4 mM, less than or equal to about 3 mM, less than or equal to about 2 mM, less than or equal to about 1 mM, less than or equal to about 0.9 mM, less than or equal to about 0.8 mM, less than or equal to about 0.7 mM, less than or equal to about 0.6 mM, from about 0.6 mM to about 6 mM, from about 0.6 mM to about 5 mM, from about 0.6 mM to about 4 mM, from about 0.6 mM to about 3 mM, from about 0.6 mM to about 2 mM, and/or from about 0.6 mM to about 1 mM. In certain embodiments, the cancer therapeutic agent is a hydrophobic cancer therapeutic agent other than a taxane. In certain embodiments, the cancer therapeutic agent is a hydrophobic cancer therapeutic agent other than paclitaxel.

The nanoparticles can include other materials (i.e., in addition to the glyceryl mono fatty acid ester, chitosan, and cancer therapeutic agent discussed above). Such other materials include those which aid in formation of the nanoparticle as well as those which affect the nanoparticles' stability once it is formed. Illustratively, the nanoparticles can include emulsifiers (e.g., polyvinyl alcohol or D-alpha-tocopheryl polyethylene glycol 1000 succinate (("vitamin E TPGS")) and/or acids (e.g., citric acid) which may have been used in their preparation and which may or may not have a role in the nanoparticles' stability. Such other materials also include those materials which are biologically active, e.g., biologically active materials which are to be delivered together with the cancer therapeutic agent. Suitable other biologically active materials that can be included in the nanoparticles of the present invention are, for example, analgesics (e.g., morphine and morphine congeners, opioid analgesics, non-opioid analgesics, and the like).

The pharmaceutical composition can be substantially free of other components, for example, as in the case where the pharmaceutical composition comprises nanoparticles in the form of a dry powder (e.g., a lyophilized free-flowing powder). Alternatively, the pharmaceutical composition can further include other components (i.e., in addition to the nanoparticles discussed above), such as commonly employed pharmaceutically acceptable excipients, diluents, stabilizers, preservatives, and the like. Selection of such other materials that can be used in the pharmaceutical compositions of the present invention will depend on a number of factors, such as route of administration, packaging considerations, and the like. For example, in certain embodiments, the pharmaceutical composition can further include (i.e., in addition to the nanoparticles discussed above) a pharmaceutically acceptable buffer or other aqueous medium in which the nanoparticles are suspended or otherwise dispersed (e.g., a pharmaceutically acceptable buffer or other aqueous medium suitable for parenteral and/or intravenous administration to a subject, such as a human or other mammal).

In certain embodiments, the nanoparticles are formed of a hydrophobic core and a hydrophilic surface layer surrounding the hydrophobic core. The hydrophobic core includes the glyceryl mono fatty acid ester, and the hydrophilic surface layer includes the chitosan. In certain embodiments, the cancer therapeutic agent is hydrophobic, and the hydrophobic core comprises the hydrophobic cancer therapeutic agent. For purposes of the present invention, the hydrophobic core is to be deemed to comprise the hydrophobic cancer therapeutic agent if a substantial portion (e.g., more than about 50%, such as more than about 60%, more than about 70%, more than about 75%, more than about 80%, more than about 85%, more than about 90%, more than about 95%, etc.) of the hydrophobic cancer therapeutic agent present in the nanoparticle is present in the hydrophobic core.

The aforementioned nanoparticles can be prepared by any suitable method. One such method, to which the present application also relates, is described below.

The present invention, in another aspect thereof, relates to a method for preparing a pharmaceutical composition in accordance with the present invention. The method includes providing a glyceryl mono fatty acid ester in a liquid state; incorporating a cancer therapeutic agent into the liquid glyceryl mono fatty acid ester to form a mixture; emulsifying the mixture in an aqueous solution comprising an emulsifier to form a water-in-oil emulsion; further emulsifying the water-in-oil emulsion in an aqueous acidic solution comprising a chitosan to form a multiple oil-water emulsion; and lyophilizing the multiple oil-water emulsion under conditions effective to produce a nanoparticulate dry powder.

As noted above, the method includes providing a glyceryl mono fatty acid ester in a liquid state. Suitable glyceryl mono fatty acid esters include those mentioned above, such as glyceryl monooleate or oleyl glycerate. Depending on ambient temperature and the particular glyceryl mono fatty acid ester (or particular combination of glyceryl mono fatty acid esters) being employed, the glyceryl mono fatty acid esters may be in liquid state or solid state. If the glyceryl mono fatty acid ester in a liquid state, no further action is needed. If in a solid or semi-solid state, the glyceryl mono fatty acid ester can be heated (e.g., at or just above its melting point) to produce liquid-state glyceryl mono fatty acid ester.

The method further includes incorporating the cancer therapeutic agent into the liquid glyceryl mono fatty acid ester to form a mixture. Suitable cancer therapeutic agents include those described above. For example, in certain embodiments, the cancer therapeutic agents is hydrophobic. The cancer therapeutic agent (or combination of same) is then dissolved, suspended, dispersed or otherwise incorporated into the liquid glyceryl mono fatty acid ester, for example, by stirring at room temperature for from 5 minutes to 2 days. The amount of cancer therapeutic agent used will depend on the particular cancer therapeutic agent being used, the particular glyceryl mono fatty acid ester being used, the cancer therapeutic agent's solubility in the particular glyceryl mono fatty acid ester being used; the desired concentration, and the like. Suitable concentrations of cancer therapeutic agent in the glyceryl mono fatty acid ester are from about 0.1% to about 50% (e.g., from about 0.2% to about 25%, from about 0.4% to about 15%, from about 0.5% to about 10%, and/or from about 1% to about 5%), by weight (w/w).

The method further includes emulsifying the mixture in an aqueous solution to form a water-in-oil emulsion. The aqueous solution includes an emulsifier, such as D-alpha-tocopheryl polyethylene glycol 1000 succinate ("vitamin E TPGS") polyvinyl alcohol (e.g., polyvinyl alcohol have a molecular weight of 30,000 to 70,000). The concentration of emulsifier can be, for example, from about 0.1% to about 5% (such as from about 0.1% to about 2.5%, from about 0.2% to about 1%, and/or about 0.5%). Suitable concentrations of the cancer therapeutic agent/glyceryl mono fatty acid ester mixture in the aqueous emulsifier solution are from about 3% to about 50% (e.g., from about 5% to about 25%, from about 10% to about 20%, from about 12% to about 18%, about 15%), by volume (v/v). Emulsification can be carried out using any suitable method, for example by ultrasonication (e.g., a Sonicator 3000 available from Misonix, Farmingdale, N.Y.) for from about 10 seconds to about 1 hour (e.g., for from about 1 minute to about 20 minutes or for about 2 minutes) at from about 2 to about 200 watts (e.g., at from about 10 to about 40 watts or at about 20 watts).

The resulting water-in-oil emulsion is then further emulsified in an aqueous acidic solution that includes a chitosan to form a multiple oil-water emulsion. Examples of suitable chitosans include those discussed above. The aqueous acidic solution can be prepared by dissolving the chitosan in a mixture of water and acid. Typically, a strong organic acid is used (e.g., citric acid or an acid having comparable acidity), and the acid is present at in a acid:chitosan weight ratio of about 1:1 or less, such as about 0.5:1 or less, about 0.2:1 or less, about 0.1:1 or less, about 0.05:1 or less, from about 0.05:1 to about 1:1, etc. Suitable concentrations of chitosan in the aqueous acidic solution are from about 0.5% to about 10% (e.g., from about 1% to about 5% or about 2.5%), weight-to-volume (w/v). Emulsification can be carried out using any suitable method, for example by ultrasonication (e.g., a Sonicator 3000 available from Misonix, Farmingdale, N.Y.) for from about 10 seconds to about 1 hour (e.g., for from about 1 minute to about 20 minutes or for about 2 minutes) at from about 2 to about 200 watts (e.g., at from about 10 to about 40 watts or at about 20 watts).

The resulting multiple oil-water emulsion is then lyophilized under conditions effective to produce a nanoparticulate dry powder, for example, at about −50° C. under suitable vacuum (e.g., less than about 0.1 mBar or at or below about 0.056 mBar pressure). In certain embodiments, the multiple oil-water emulsion is frozen (e.g., in a dry ice bath at about −80° C.) prior to being lyophilized. In certain embodiments, the multiple oil-water emulsion is centrifuged or filtered and then frozen (e.g., in a dry ice bath at about −80° C.) prior to being lyophilized. In certain embodiments, the multiple oil-water emulsion is centrifuged or filtered prior to being lyophilized.

The resulting dry powder can be stored for later use, at which time it can be reconstituted in a pharmaceutically acceptable aqueous medium, for example by suspending or otherwise dispersing the resulting dry powder in the pharmaceutically acceptable aqueous medium. Examples of suitable pharmaceutically acceptable aqueous media include a saline buffers (e.g., phosphate buffered saline ("PBS")), and other pharmaceutically acceptable buffers.

The aforementioned pharmaceutical compositions of the present invention can be used, for example, to treat cancer in a subject by first providing one of the aforementioned pharmaceutical compositions and then administering the pharmaceutical composition to the subject.

In certain embodiments, the pharmaceutical compositions is provided in the form of a dry powder; and the method further includes reconstituting the dry powder in PBS or another pharmaceutically acceptable aqueous medium prior to administration.

The composition can be administered parenterally, intravenously, or by any other suitable route.

In one illustrative embodiment, the pharmaceutical compositions are administered parenterally by injecting the composition close to the site of a tumor. As used herein, "close to the site of a tumor" is meant to refer to local targeting and delivery of the composition to the site of the tumor and is meant to include direct injection into the tumor as well as injection within about 1 cm (e.g., within 1 cm, within about 5 mm, within 5 mm, within about 2 mm, within 2 mm, etc.) of the tumor. The pharmaceutical composition can be administered, for example, via a single injection or via multiple injections, such as in the case where the pharmaceutical composition is administered by injecting it both into the tumor and around the periphery of the tumor.

In another illustrative embodiment, pharmaceutical compositions are administered systemically to the subject, for example, as in the case where the pharmaceutical compositions are administered intravenously, such as by injecting the composition into the subject's circulatory system.

In another illustrative embodiment, the pharmaceutical compositions are administered enterally, for example, to irrigate a tumor in the gastrointestinal tract.

It is envisioned that a number of cancers can be treated using the method of the present invention. Illustratively, the cancer can be one in which transmembrane mucin glycoproteins are overexpressed, such as breast cancer and colon cancer. These and other cancers in which transmembrane mucin glycoproteins are overexpressed include pancreatic ductal carcinoma (as discussed, e.g., in Chhieng et al., "MUC1 and MUC2 Expression in Pancreatic Ductal Carcinoma Obtained by Fine-Needle Aspiration," *Cancer*, 99(6):365-371 (2003), which is hereby incorporated by reference), human colon cancers (as discussed, e.g., in Sternberg et al., "Alternative Splicing of the Human MUC2 Gene," *Arch. Biochem. Biophys.*, 421(1):21-33 (2004), which is hereby incorporated by reference), papillary thyroid carcinoma (as discussed, e.g., in Magro et al., "Differential Expression of Mucins 1-6 in Papillary Thyroid Carcinoma: Evidence for Transformation-Dependent Post-Translational Modifications of MUC1 In situ," *Arch. Biochem. Biophys.*, 421(1):21-33 (2004), which is hereby incorporated by reference), human ovarian carcinomas (as discussed, e.g., in Feng et al., "Expression of MUC1 and MUC2 Mucin Gene Products in Human Ovarian Carcinomas," *Jpn. J. Clin. Oncol.*, 32(12):525-529 (2002), which is hereby incorporated by reference), respiratory carcinomas (as discussed, e.g., in Berger et al., "Respiratory Carcinoma Cell Lines. MUC Genes and Glycoconjugates," *Am. J. Respir. Cell Mol. Biol.*, 20(3):500-510 (1999), which is hereby incorporated by reference), prostate cancers, skin cancers, testicular cancers, oral cancers, and the like. "Subject", as used herein, is meant to include humans and other mammals, examples of which are humans suffering from breast cancer, pancreatic cancer, colon cancer, prostate cancer, lung cancer, skin cancer, ovarian cancer, uterine cancer, testicular cancer, oral cancer, and/or other types of cancers, such as other cancers in which transmembrane mucin glycoproteins are overexpressed.

While not intending to be bound by any mechanism by with the above pharmaceutical compositions and methods may operate, it is believed that the nanoparticles have mucoadhesive properties; that the mucoadhesive properties increase the effect of the therapeutic agent on cancer cells in the sample; that this increased therapeutic effect may be due to the nanoparticles' interaction with increased (relative to the non-cancer cells) levels of mucin on and/or around the cancer cells; and that, in this manner, the therapeutic agent can be made to selectively or preferentially target cancer cells (relative to non-cancer cells).

While the above nanoparticles, pharmaceutical compositions, and methods have focused on the use of chitosan, it should be noted that the chitosan can be replaced (in whole or in part) with carbopols, carbomers, and combinations thereof. With regard to the use of carbopols, it should be noted that carbopols are generally not biodegradable and, therefore, formulations containing carbopols may not be suitable for administration by parenteral or intravenous injection. However, they can be used for treatment of the gastrointestinal tract, e.g., by injection or other route of enteral administration to irrigate the gastrointestinal tract).

It will be appreciated that the actual preferred amount of pharmaceutical composition to be administered according to the treatment methods of the present invention will vary according to the particular cancer therapeutic agent being employed, the particular composition formulated, and the mode of administration. Many factors that may modify the action of the composition (e.g., body weight, sex, diet, time of administration, route of administration, rate of metabolism, condition of the subject, drug combinations, and reaction sensitivities and severities) can be taken into account by those skilled in the art. Administration can be carried out in a single dose (e.g., one parental or intravenous injection or irrigation or multiple injections or irrigations all at one time) or in multiple doses (e.g., periodic injections or irrigations) within the maximum tolerated dose. Optimal administration rates for a given set of conditions can be ascertained by those skilled in the art using conventional dosage administration tests.

The present invention is further illustrated by the following examples.

EXAMPLES

Example 1

Physiochemical Characterization of a Nanoparticulate Drug Delivery System

In this Example 1 and those which follow, we describe a formulation for a new nanoparticulate drug delivery system ("nDDS") that contains chitosan and glyceryl monooleate ("GMO") for the delivery of a wide variety of drugs to overcome major obstacles like poor solubility, poor bioavailability and P-gp mediated efflux. It was thought that formulation might overcome some or all of these obstacles through the bioadhesion of the nDDS to mucin-1 antigen that is overexpressed and under glycosylated on almost all human adenocarcinomas and facilitate an increased cellular and intracellular drug association.

Briefly, the research described in this Example 1 and those which follow provides a proof of concept that these two biomaterials can be co-formulated to yield polycationic nano-sized particles that typically range in diameter from 400 to 700 nm with the therapeutic agent entrapped, absorbed, chemically coupled, or otherwise disposed in one or both of the bio-polymeric matrices. It is believed that the co-formulated chitosan/GMO nDDS provides bioadhesive properties to increase the cellular association of encapsulated drug and provides sustained release of the drug. In addition, the Examples show increased cellular association of encapsulated drug and sustained delivery corresponds to increased effectiveness of paclitaxel ("PTX") in human breast cancer cells (MDA-MB-231). There is some evidence to show that the nanoparticles have a hydrophobic inner-core surrounded by a hydrophilic surface coating that exhibits a significant positive charge. The nanoparticles can be stored as a lyophilized powder and easily re-suspended in an aqueous medium. The highly positive surface charge of the nDDS is believed to aid in the mucoadhesive properties to adhere to the carbohydrates/glycoconjugate sites over-expressed on cancerous cells. Together, the mucoadhesive properties of chitosan and the over expression of mucin-1 antigen in human adenocarcinomas may make a drug delivery system formulated with chitosan/GMO an valuable for anti-cancer therapy.

Example 2

Methods and Materials

Paclitaxel ("PTX") was purchased from InB:HauserPharmaceutical Services Inc. (Denver, Colo.). MDA-MB-231 breast cancer cell line was purchased from American Type Culture Collection (ATCC) (Manassas, Va.). Gibco brand cell culture media and constituents, RPMI 1640, fetal bovine serum ("FBS"), penicillin/streptomycin, trypsin-EDTA, and L-glutamine were purchased from Invitrogen (Carlsbad, Calif.). Glyceryl monooleate ("GMO") was obtained from Eastman Chemical Company (Kingsport, Tenn.). Anhydrous citric acid was purchased from Acros Organics (Fairlawn, N.J.). Acetonitrile (HPLC), methanol (HPLC), ammonium acetate (HPLC), sodium phosphate monobasic, sodium phosphate dibasic, hydrochloric acid (reagent grade), Triton-X-100, THERMANOX™ slides, and Falcon tissue culture flasks and plates were purchased from Fisher Scientific (Fairlawn, N.J.). TWEEN™-80 ("T-80") (polyoxyethylene sorbitan monooleate) and sodium chloride were purchased from Sigma Chemical Company (St. Louis, Mo.). Low molecular weight chitosan was purchased from Aldrich Chemical Company (Milwaukee, Wis.).

Nanoparticles were prepared according to the following typical procedure. Briefly, the nDDS was prepared by a multiple water-in-oil emulsion and solvent evaporation method. GMO was melted (40° C.) to achieve a fluid phase, and an amount of PTX (4.5% w/w/w), dexamethasone ("DEX") (4.5% w/w/w), or osmium tetroxide (1.0% w/w/w) (an electron dense compound for transmission or scanning electron microscopy) was incorporated into the fluid phase of GMO. An emulsion comprised of the GMO mixture (14% v/v) and an emulsifier consisting of 0.5% aqueous polyvinyl alcohol (MW 30000-70000) was ultrasonicated for 2 minutes at 18 watts (Sonicator 3000, Misonix, Farmingdale, N.Y.). The water-in-oil emulsion thus formed was further emulsified in a solution of chitosan (2.4% w/v) dissolved in citric acid (2.4% w/v) and ultrasonicated for 2 minutes at 18 watts. The final multiple oil-water emulsion was frozen (−80° C.) prior to freeze drying (−52° C. and <0.056 mBar pressure) (FreeZone, Labconco, St Louis, Mo.).

The nanoparticles were characterized as follows. Mean particle size, size distribution, and mean zeta potential of the nanoparticles were determined using a zetameter (ZetaPlus, Brookhaven Instruments Corporation, Holtsville, N.Y.). Briefly, the nanoparticles were resuspended in deionized water (0.4 mg/ml) in triplicate and analyzed for particle size and zeta potential. In addition, the particle size distribution and morphological microstructure were also visualized utilizing transmission electron microscopy ("TEM") methods described in Panyam et al., "Targeting intracellular targets," Curr. Drug Deliv., 1(3):235-247 (2004), which is hereby incorporated by reference. Briefly, the osmium tetroxide loaded nanoparticles were resuspended in deionized water (1 mg/ml) and placed (about 20 μl) on FORMVAR™-coated copper grids (150 mesh, Ted Pella Inc., Redding, Calif.) and allowed to air-dry at room atmospheric conditions. The dried grids were visualized using TEM (JEM-1011, Japan).

The percent nanoparticle yield was calculated as a ratio of weight of lyophilized nanoparticulate powder to total weight of all the formulation constituents. The percent drug loading was calculated and expressed as a ratio of amount of drug extracted from the polymer matrix to the total weight of the nanoparticles. The encapsulation efficiency was calculated and expressed as a ratio of weight of drug present in a batch of nanoparticle to the weight of drug used in the formulation. Briefly, approximately 10 mg of accurately weighted lyophilized nanoparticles were dispersed in an organic solvent (15 ml, 60:40 v/v acetonitrile and water) and sonicated (Fisher Scientific FS 20, Fairlawn, N.J.) for 4 hours to extract either PTX or DEX for HPLC analysis (Shimadzu SP-10A VP, Columbia, Md.). The HPLC analysis for PTX was achieved on a C18 ZORBAX™ column (150×4.6 mm, 5 μm) (Phenomenex, Torrance, Calif.) with a mobile phase consisting of acetonitrile, methanol, 0.1M ammonium acetate (48.5: 16.5:35% v/v/v) at a flow rate of 0.75 ml/min. The effluents were monitored at 227 nm and quantified using the area under the peak from standard solutions dissolved in mobile phase (0.4 to 2 μg/ml). The HPLC analysis for DEX was achieved on a C18 luna column (4.6 mm, 250 mm, 5 μm) (Phenomenex, Torrance, Calif.). The mobile phase for DEX was methanol/0.1M ammonium acetate 60:40 (v/v) at flow rate of 1.2 ml/min. The effluents were monitored at 254 nm and quantified using the area under the peak from standard solutions dissolved in mobile phase (2 to 10 µg/ml).

The in vitro drug release profiles of different nanoparticle formulations were determined by measuring the cumulative amount of drug released from the nanoparticle over predetermined time intervals. Briefly, a known quantity of the formulation (2 to 10 mg) was dispersed in 40 ml of PBS (pH 7.4) in a capped Erlenmeyer flask in triplicate, agitated in a water bath incubator at 37° C. and 80 rpm. At predetermined time intervals (5 to 240 min for PTX and 5 to 270 min for DEX), 200 µl of the sample was withdrawn with a filter tip needle and replaced with an equal amount of PBS. In simultaneous studies, equal amounts of the formulations were dispersed in 15 ml of acetontrile:water (60:40 v/v) and sonicated for 4 hours to extract the total drug. In separate studies, the in vitro release of PTX was determined in the presence or absence of 0.02% (v/v) T-80 by the same methods. The samples were suitably diluted before determining the drug concentration of PTX or DEX by HPLC as previously above.

The physical state of the drug in the formulation was evaluated by x-ray powder diffractometry methods as described in Dash et al., "X-Ray Powder Diffractometric Method for Quantitation of Crystalline Drug in Microparticulate Systems. I. Microspheres," *J. Pharm. Sci.*, 91(4):983-990 (2002), which is hereby incorporated by reference. Briefly, the blank nanoparticles and the nanoparticle formulations containing PTX or DEX were filled into a cavity-mount quartz holder with an aluminum sample holder. The samples were exposed to CuK-alpha radiation (40 kV and 30 mA) on an x-ray diffractometer (Rigaku D-Max/B Horizontal Q/2Q, Texas). The nanoparticle formulations were also analyzed by differential scanning calorimetry ("DSC"). DSC thermograms were obtained for pure drugs, drug loaded nanoparticles, and blank nanoparticles. The lyophilized samples were weighed (0.3 mg) and sealed into aluminum crimp pans, and an empty pan was used as a reference. The samples were heated at the rate of 10° C./min, between 23 and 300° C. in a DSC apparatus (Shimadzu DSC-60, Columbia, Md.) connected to a thermal data analysis system. The thermograms were analyzed after each run was performed.

The in vitro bioadhesion and cellular uptake of the chitosan/GMO nanoparticle delivery system were evaluated in MDA-MB-231 human breast cancer cells. For the bioadhesion studies, MDA-MB-231 cells were seeded on THERMANOX™ cover-slips placed in Falcon 6-well tissue culture plates at a density of approximately 150,000 cells per cover-slip and incubated for 24 hours in a humidified chamber at 37° C. in RPMI-1640 growth media supplemented with 10% FBS, 1% L-glutamine, and 1% penicillin/streptomycin. Lyophilized osmium tetroxide loaded nanoparticles (1 mg/ml) were reconstituted in assay II buffer (122 mM sodium chloride, 3 mM potassium chloride, 25 mM sodium bicarbonate, 0.4 mM sodium phosphate di-basic, 1.4 mM calcium chloride, 1.2 mM magnesium sulfate, 10 mM HEPES, 10 mM glucose) adjusted to pH 7.4. The cell monolayers were exposed to the freshly dispersed osmium tetroxide nanoparticles for various times (15 to 30 min) in a humidified chamber at 37° C. After the exposure period, the cell monolayers were washed three times in ice cold PBS, fixed with a PBS buffered glutaraldehyde solution (3% v/v), and dehydrated with successive alcohol solutions (50-to-100 percent) for 10 minutes prior to mounting on a stub for critical point drying with carbon dioxide and gold sputter coating in an argon matrix for scanning electron microscopy ("SEM") imaging. The mounted cell monolayers were visualized using SEM (JEOL-840A, Japan).

The cellular association of the nanoparticle delivery system in MDA-MB-231 human breast cancer cells was also analytically evaluated by the HPLC method previously mentioned. In these studies, the cell monolayers were cultured in standard 6-well tissue culture plates at a seeding density of 500,000 cells per square centimeter and cultured until confluency in a humidified chamber at 37° C. in RPMI-1640 growth media supplemented with 10% FBS, 1% L-glutamine, and 1% penicillin/streptomycin. Confluent cell monolayers were treated with a single bolus solution of paclitaxel (1 µM) or the nanoparticulate delivery system loaded with paclitaxel (free fraction 1 µM) in assay buffer II for various times (15 to 45 minutes). The cell monolayers were washed three times with ice cold PBS and lysed with 1% Triton-X-100. The cell monolayer lysates were collected in a microcentrifuge tube, and a sample (25 µl) was assayed for total protein content by the BCA protein assay (Pierce, Rockford, Ill.). The remaining cell lysates were frozen (−80° C.) prior to freeze-drying (−52° C. and <0.056 mBar pressure) (FreeZone, Labconco, Kansas City, Mo.). The freeze-dried cell monolayer lysates were re-suspended in acetonitrile, agitated 100 rpm for 30 minutes at 37° C. in an incubated shaker (Orbit, Labline Instruments Inc., Melrose Park, Ill.). The microcentrifuge tubes were centrifuged at 14,000 RPM in a microcentrifuge for 5 minutes at 4° C. (ACCUSPIN™ Micro R, Fisher Scientific, Fairlawn, N.J.), and the amount of paclitaxel was determined in supernatant by HPLC methods. The cellular uptake was calculated as a ratio of the amount paclitaxel per mg total cellular protein.

Cytotoxicity profile studies of the chitosan/GMO nanoparticles were carried out as follows. The viability of MDA-MB-231 human breast cancer cells were determined using MTT cytotoxicity analysis. Briefly, the cells were seeded in a 24-well cell culture plate at a density of 20,000 cells per well in 1000 µl of growth media and incubated overnight in a humidified chamber at 37° C. in RPMI-1640 growth media supplemented with 10% FBS, 1% L-glutamine, and 1% penicillin/streptomycin. The cells were treated with various concentrations (0.001 to 100 µM) in a single bolus with a solution of PTX or the nanoparticulate delivery system loaded with and without 4.5% (w/w) PTX (0.001 to 100 µM) or with 4.5% (w/w) DEX (0.001 to 100 µM) for 4 hours, then washed three times with PBS (pH 7.4) and supplied with fresh growth media (48-to-96 hours). After the incubation period, the cells were treated with fresh MTT reagent (250 µL, 5 mg/ml) and further incubated for 4 hours, then treated with a fresh solvent consisting of 20% (w/v) SDS dissolved in water at 37° C. mixed with an equal volume of dimethyl formamide ("DMF"). The solvent pH was adjusted to 7.4 using 2.5% of 80% acetic acid and 1% of 1N HCl. The absorbance was read on a microplate reader at 550 nm. The absorbance data were analyzed and presented as percent survival of control monolayers receiving media alone.

Statistical analyses were performed and the results are expressed as mean±standard error of the mean ("SEM") for all quantitative data. The analytical cellular association data was statistically analyzed using single factor analysis of variance followed by Tukey multiple post hoc test for paired comparisons of means (SPSS 10, SPSS Inc., Chicago, Ill.). For all studies, statistical significance was designated as p<0.05, unless otherwise stated.

Example 3

Results and Discussion Regarding Nanoparticle Characterization

The physiochemical characteristics of chitosan/GMO nanoparticle formulations containing blank, PTX, DEX, and osmium tetroxide are summarized in Table 1.

TABLE 1

| Nanoparticle Preparation Chitosan/GMO | Particle Size (nm) | Particle Charge (mV) | Percent Yield | Percent LE | Percent EE |
| --- | --- | --- | --- | --- | --- |
| Blank | 676.0 ± 16.3 | +31.78 ± 0.54 | 99.7 ± 0.17 | n/d | n/d |
| Osmium tetroxide | 532.2 ± 39.3 | +25.33 ± 1.46 | n/d | n/d | n/d |
| 4.5% DEX | 454.5 ± 43.7 | +26.66 ± 0.87 | 99.4 ± 0.32 | 4.5 ± 0.05 | 99.5 ± 0.17 |
| 4.5% PTX | 432.5 ± 37.1 | +33.17 ± 1.52 | 98.8 ± 0.76 | 4.5 ± 0.03 | 98.9 ± 0.83 |

Values are mean ± SEM, n = 3
Yield = weight of lyophilized nanoparticles/weight of formulation constituents
Loading Efficiency (LE) = amount of drug extracted/weight of nanoparticles
Entrapment Efficiency (EE) = weight of drug present in a batch/weight of drug used
Not determined (n/d)

The mean particle size ranged from 676 nm (blank) to 435.5 nm (PTX). The mean size distribution appears to be inversely proportional to the hydrophobicity of the compound incorporated into the polymeric matrix, suggesting that increasing the hydrophobicity of the drug encapsulated decreases the hydrodynamic volume of the nanoparticle by tightly packing the hydrophobic tails of GMO. Although the mean particle size distribution decreased, there was no significant change in the surface charge distribution. The particle surface charge distribution ranged from 25.33 mV (osmium tetroxide) to 33.17 mV (PTX). The positive surface charge is indicative that chitosan is organized at the surface of the nanoparticle. However, there appears to be a slight inverse correlation between the decrease in hydrodynamic volume and the increase in particle surface charge, with the exception of the blank nanoparticles. This inverse relationship is suggestive that chitosan becomes more uniformly organized as the hydrophobic tails of GMO become more tightly packed. The mean percent yield was found to be near 100 percent with a low of 98.8 (PTX) to high of 99.7 (blank). The drug loading efficiency and encapsulation efficiency was also near 100 percent, similar to the percent yield. This was surprising, given that chitosan nanoparticles have an entrapment efficiency of cyclosporine A (hydrophobic drug like PTX) of 74% (De Campos et al., "Chitosan Nanoparticles: A New Vehicle for the Improvement of the Delivery of Drugs to the Ocular Surface. Application to Cyclosporin A," Int. J. Pharm., 224(1-2):159-168 (2001), which is hereby incorporated by reference). The entrapment efficiency of chitosan is dependent on many factors such as molecular weight of chitosan used, concentration of the drug molecules, and pH of the formulation (Wu et al., "Chitosan Nanoparticles as a Novel Delivery System for Ammonium Glycyrrhizinate," Int. J. Pharm., 295(1-2):235-245 (2005) ("Wu"), which is hereby incorporated by reference). Chitosan molecules basically interact with drug molecules by Van der Waals forces, like electrostatic force, hydrogen bonding, and hydrophobic interactions. The encapsulation efficiency of chitosan nanoparticles has been shown to be inversely proportional to chitosan concentration and viscosity and drug concentration (Wu, which is hereby incorporated by reference). To increase the loading efficiency of hydrophobic drugs and control the release of drug from various chitosan nanoparticle preparations, others have increased the hydrophobicity of chitosan with covalent modifications (Jeong et al., "Polyion Complex Micelles Composed of All-Trans Retinoic Acid and Poly (Ethylene Glycol)-Grafted-Chitosan," J. Pharm. Sci., 95(11): 2348-2360 (2006) ("Jeong"); Hu et al., "Shell Cross-Linked Stearic Acid Grafted Chitosan Oligosaccharide Self-Aggregated Micelles for Controlled Release of Paclitaxel," Colloids Surf. B Biointerfaces, 50(2):97-103 (2006) ("Hu"); Kim et al., "Hydrophobically Modified Glycol Chitosan Nanoparticles as Carriers for Paclitaxel," J. Control. Release, 111(1-2):228-234 (2006); Maestrelli et al., "A New Drug Nanocarrier Consisting of Chitosan and Hydroxypropylcyclodextrin," Eur. J. Pharm. Biopharm., 63(2):79-86 (2006) ("Maestrelli"); and Agnihotri et al., "Recent Advances on Chitosan-Based Micro- and Nanoparticles in Drug Delivery," J. Control. Release, 100(1):5-28 (2004), which are hereby incorporated by reference). Stearic acid grafted chitosan oligonucleotide self aggregated micelles have been used to develop higher entrapment efficiencies (94%) for paclitaxel (Hu, which is hereby incorporated by reference). In addition, complexation of hydrophobic drugs, like furosemide, with cyclodextrins has been shown to increase their entrapment efficiency 4- to 10-fold in chitosan nanoparticles (Maestrelli, which is hereby incorporated by reference). Furthermore, studies have used solid triglycerides and polyethylene glycol (PEG) cores for chitosan surface modified nanocapsules to increase the loading efficiency (64% to 94%) of hydrophobic drugs for oral administration (Prego et al., "Chitosan-PEG Nanocapsules as New Carriers for Oral Peptide Delivery. Effect of Chitosan Pegylation Degree," J. Control. Release, 111(3):299-308 (2006); and Garcia-Fuentes et al., "A Comparative Study of the Potential of Solid Triglyceride Nanostructures Coated with Chitosan or Poly(Ethylene Glycol) as Carriers for Oral Calcitonin Delivery," Eur. J. Pharm. Sci., 25(1):133-143 (2005), which are hereby incorporated by reference). Together, these studies indicate that the entrapment of hydrophobic drugs is not so efficient in chitosan nanoparticle preparations. While not intending to be bound by any mechanism by with the above pharmaceutical compositions and methods may operate, it is believed that, in the current study, the nanoparticle formulation utilized the self-emulsifying properties of GMO to form a hydrophobic core, presumably micellar, to enhance the solubility of PTX and provide a foundation for chitosan aggregation. The near 100 percent loading and entrapment efficiencies of PTX in this formulation are attributed to the self-emulsifying properties of GMO. Monoglycerides, like GMO, are polar lipids with poor water solubility that exhibit properties that resemble non-ionic surfactants that have been comprehensively described (Lutton, "Phase Behavior of Aqueous Systems of Monoglycerides," J. Am. Oil Chem. Soc., 42(12):1068-1070 (1965), which is hereby incorporated by reference).

Figure 1B:
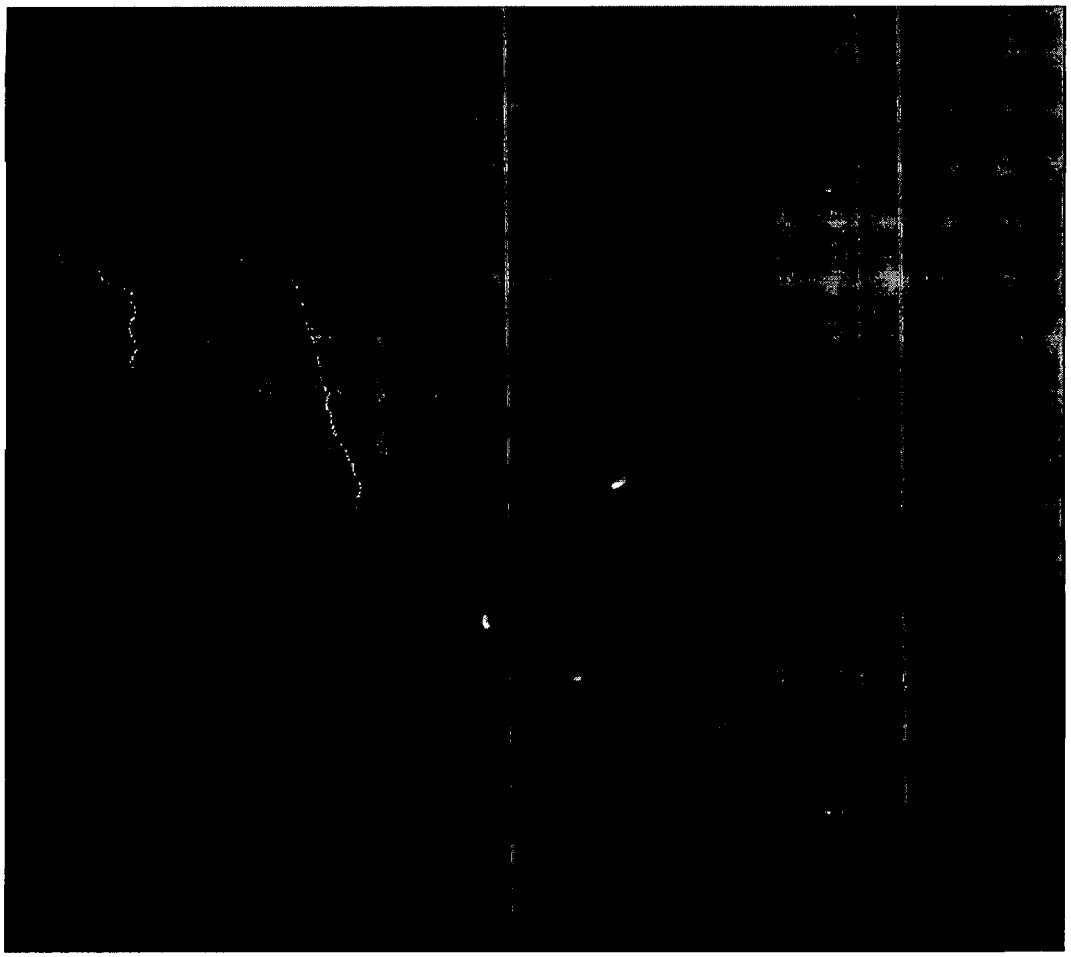

Morphology and microstructure of the nanoparticles were examined using TEM, and the results are presented in FIG. 1A (10,000×) and FIG. 1B (50,000×). The TEM images of the osmium tetroxide nanoparticles revealed a heterogenous size distribution (FIG. 1A). The nanoparticles also appear to suspend in an aqueous environment as individual particles with a spherical to elliptical shape. In addition, the absence of osmium tetroxide in the inner core of the nanoparticles clearly provides evidence that the microstructure of the nanoparticles consists of a hydrophobic inner core consisting of GMO surrounded by a hydrophilic surface layer consisting of chitosan. TEM images acquired at higher magnification show the particle surface morphology to be smooth and non-porous in nature, suggesting that they may have a nano-sized gel forming nature in an aqueous environment (FIG. 1B). Together, these data clearly provide evidence that nanoparticles consisting of chitosan/GMO can be lyophilized and reconstituted in an aqueous environment without distortion of shape and size.

Figure 2:
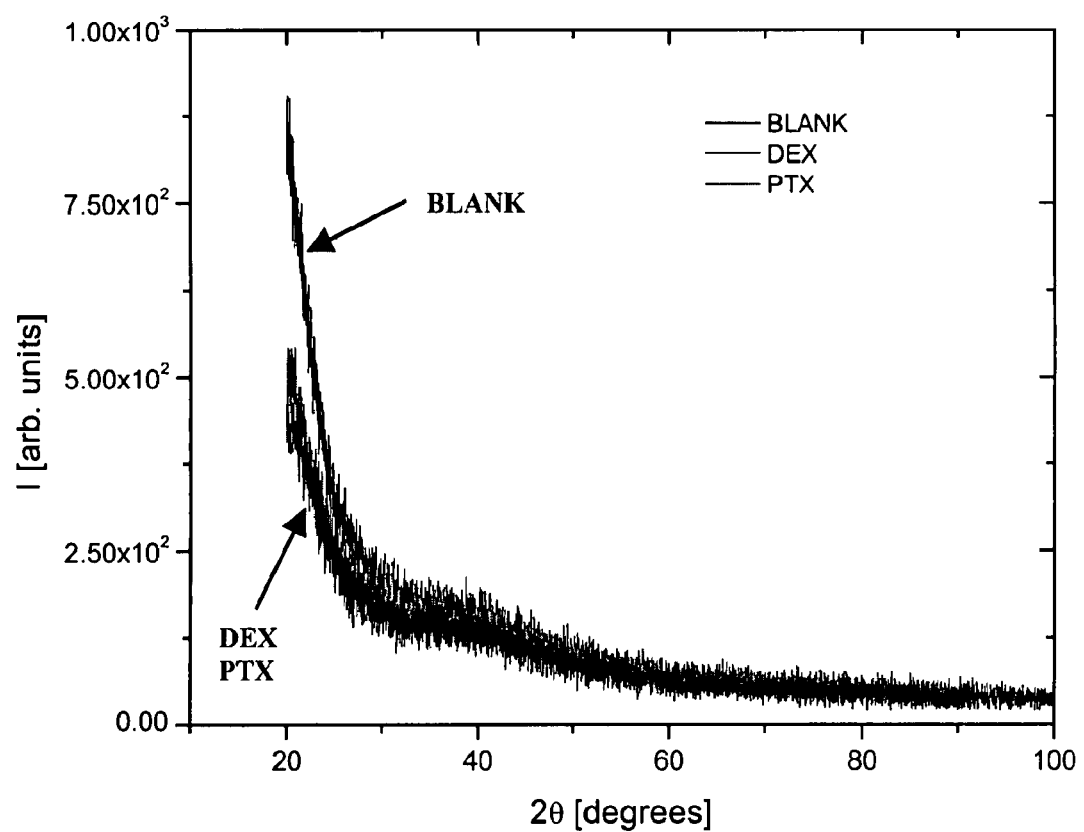
FIG. 2 is a plot of an x-ray diffraction of blank (unloaded) chitosan/GMO nanoparticles compared to chitosan/GMO nanoparticles loaded with dexamethasone ("DEX") and chitosan/GMO nanoparticles loaded with paclitaxel ("PTX") of the present invention.

The physical state of the drug in the polymeric matrix was examined using x-ray diffraction, and the results are presented in FIG. 2. The powder x-ray diffraction patterns for the drug (PTX or DEX) loaded nanoparticles was without any remarkable difference when compared to the powder x-ray pattern for blank (unloaded) nanoparticles. The lack of any remarkable diffraction patterns for the nanoparticles with PTX or DEX and without drug indicates that the drug incorporated in the nanoparticles existed in a non-crystalline state. DSC thermograms also provide further evidence by the lack of endothermic melting peaks for PTX (213° C.) or DEX (262° C.) in the nanoparticle formulations when compared to the crystalline drug alone (data not shown). In agreement with the powder x-ray pattern, the DSC thermographs further indicate that the drug incorporated in the nanoparticles existed in a non-crystalline state.

Figure 3A:
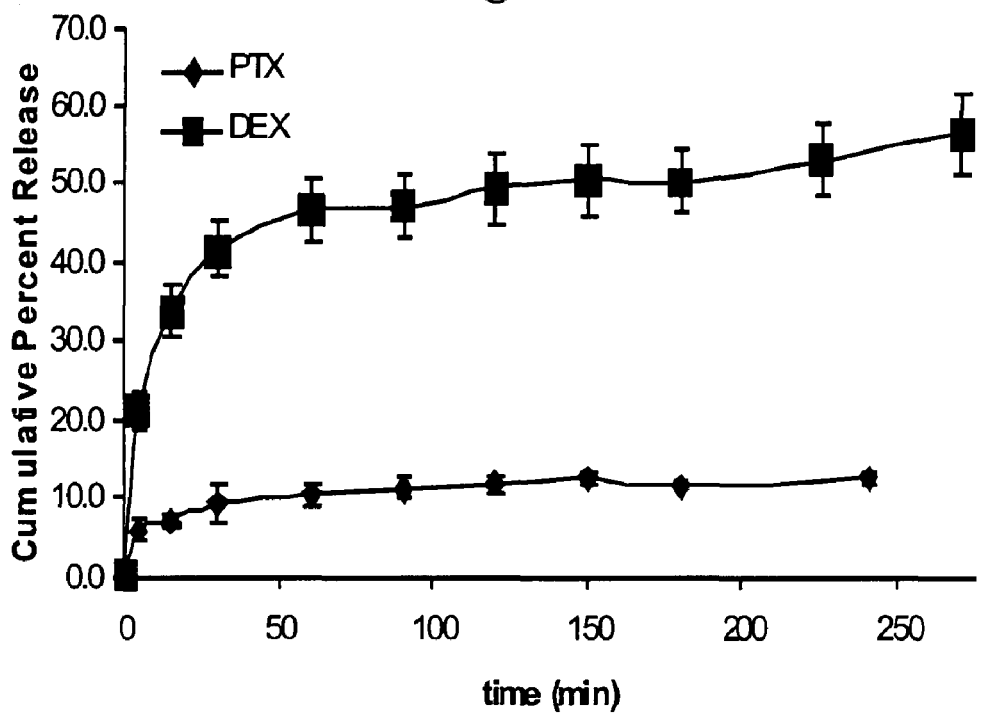
FIG. 3A is a graph showing the in vitro release profiles of PTX (closed diamonds) or DEX (closed squares) from chitosan/GMO nanoparticles of the present invention into PBS at pH 7.4 maintained at 37° C. (mean±SEM, n=3).
Figure 3B:
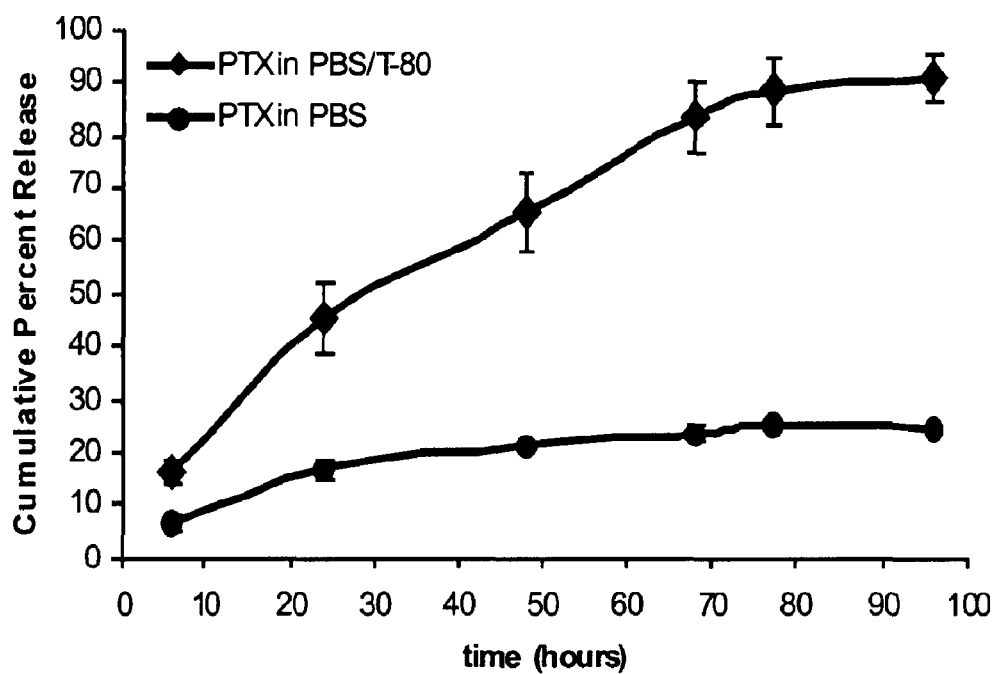
FIG. 3B is a graph showing the in vitro release profiles of PTX from chitosan/GMO nanoparticles of the present invention in the presence of TWEEN™-80 ("T-80") (closed diamonds) and in the absence of T-80 (closed circles) into PBS at pH 7.4 maintained at 37° C. (mean.±SEM, n=3).

The in vitro drug release profiles of different nanoparticle formulations and the effects of T-80 were determined by measuring the cumulative amount of drug released from the nanoparticle over predetermined time intervals. FIG. 3A shows the in vitro drug release profiles of PTX (closed diamonds) or DEX (closed squares) from chitosan/GMO nanoparticles into PBS at pH 7.4 maintained at 37° C. (mean±SEM, n=3). FIG. 3B shows the effects of T-80 on the release profile of PTX from chitosan/GMO nanoparticles in the presence of T-80 (closed diamonds) and the absence of T-80 (closed circles) into PBS at pH 7.4 maintained at 37° C. (mean±SEM, n=3). The in vitro drug release profiles for PTX and DEX showed common characteristics of burst-release initially, followed by a slow near zero-order rate of release over the experimental period. A regression analysis of the slow terminal rate of drug release for the nanoparticles observed was approximately 0.013 percent per minute ($r^2$=0.766) with a maximal of 13 percent released in 4 hours for PTX and 0.052 percent per minute ($r^2$=0.922) with a maximal of 55 percent released over a similar study period for DEX. The release profile suggests that, under sink conditions, a single dose of chitosan/GMO nanoparticles loaded with PTX or DEX would, presumably, take an estimated 4.81 days or 18.4 hours to release the entire entrapped drug from the formulation. In separate studies for a longer time period (96 hours), the release characteristics of PTX from the chitosan/GMO nanoparticles were qualitatively similar when compared to the four hour study (FIG. 3B). However, the presence of 0.02% (v/v), T-80 increased the rate and extent of PTX released from the chitosan/GMO nanoparticle formulation (FIG. 3B). The release characteristics of these drug delivery systems depend on the hydrophilicity or hydrophobicity of the drug incorporated and the water content of the medium. Monoglycerides like GMO have both hydrophobic and hydrophilic properties that have been extensively exploited as active drug delivery vehicles including liquid crystalline aggregates (liposomes and cubosomes) or cross-linked gel networks (hydrogels) (Garg et al., "Cubosomes: an Overview," *Biol. Pharm. Bull.*, 30(2):350-353 (2007); Ganguly et al., "A Novel in situ Gel for Sustained Drug Delivery and Targeting," *Int. J. Pharm.*, 276(1-2):83-92 (2004); and Sadhale et al., "Glyceryl Monooleate Cubic Phase Gel as Chemical Stability Enhancer of Cefazolin and Cefuroxime," *Pharm. Dev. Technol.*, 3(4):549-556 (1998), which are hereby incorporated by reference). When the drug is incorporated in the lipid phase, the drug has to partition between the aqueous and the lipid phase, where as drug entrapped in the aqueous channels of more complex structures would diffuse into the extracellular fluid. In the current studies, the chitosan/GMO nanoparticles demonstrated sustained release characteristics that appear to be dependent on the hydrophobicity of the therapeutic agent incorporated in the polymeric matrices. In well documented studies, the release of therapeutic agents from various polymeric matrices is dependant on concentration gradient and water penetration, as well as structural degradation (Uner, "Preparation, Characterization and Physico-Chemical Properties of Solid Lipid Nanoparticles (SLN) and Nanostructured Lipid Carriers (NLC): Their Benefits as Colloidal Drug Carrier Systems," *Pharmazie*, 61(5):375-386 (2006); Bummer, "Physical Chemical Considerations of Lipid-Based Oral Drug Delivery—Solid Lipid Nanoparticles," *Crit. Rev. Ther. Drug Carrier Syst.*, 21(1):1-20 (2004); Lockman et al., "Nanoparticle Technology for Drug Delivery Across the Blood-Brain Barrier," *Drug Dev. Ind. Pharm.*, 28(1):1-13 (2002); and Douglas et al., "Nanoparticles in Drug Delivery," *Crit. Rev. Ther. Drug Carrier Syst.*, 3(3):233-261 (1987), which are hereby incorporated by reference). In the current studies, the initial burst release of the therapeutic agent from chitosan/GMO nanoparticles is probably attributable to either surface bound moieties or a tendency of chitosan to swell in an aqueous environment, permitting increased water penetration. However, the fact that extent and terminal rate of release for DEX was higher than PTX suggests the release mechanism of the therapeutic agent from chitosan/GMO nanoparticles depends on the partitioning of therapeutic agent from the hydrophobic core to the aqueous medium, since PTX is more hydrophobic than DEX. Further indications of this release mechanism are the increased rate and the increased extent of PTX released from the chitosan/GMO nanoparticles in the presence of a surfactant (T-80) increasing the water penetration. This mechanism of release suggests that the release characteristics could be further controlled by controlling the subsequent water penetration.

Example 4

Figure 4A:
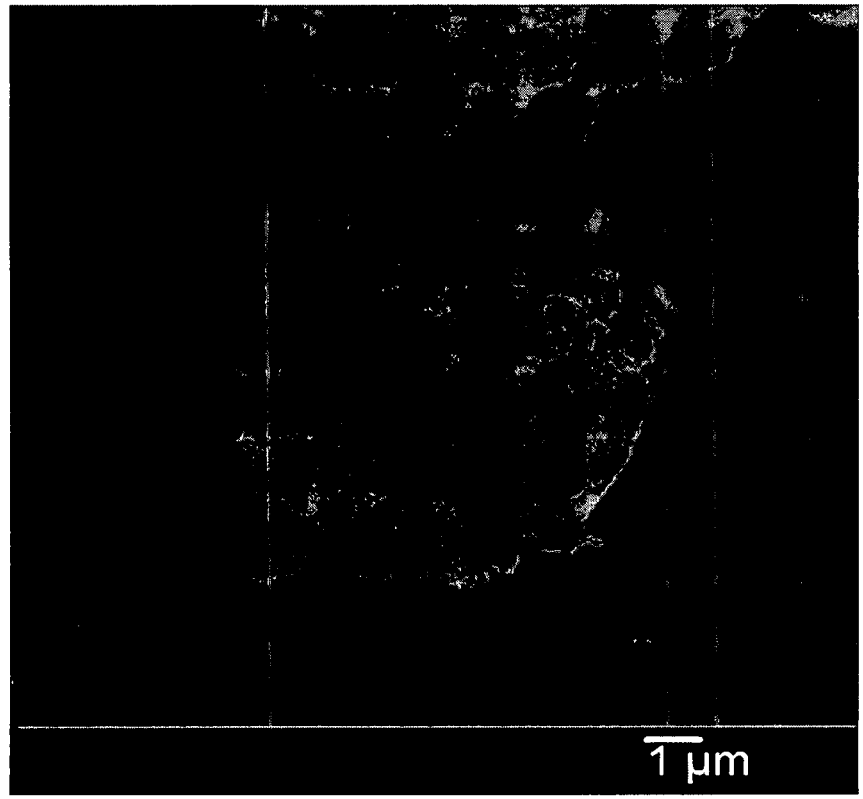
FIGS. 4A and 4B are scanning electron microscopy ("SEM") images of human breast cancer cells (MDA-MB-231) showing the bioadhesive properties of chitosan/GMO sustained release nanoparticles. The control cells were treated with the particle suspension medium alone for 30 minutes (FIG. 4A), while the test cells were treated with osmium tetroxide loaded chitosan/GMO nanoparticles for 30 minutes (FIG. 4B).
Figure 4B:
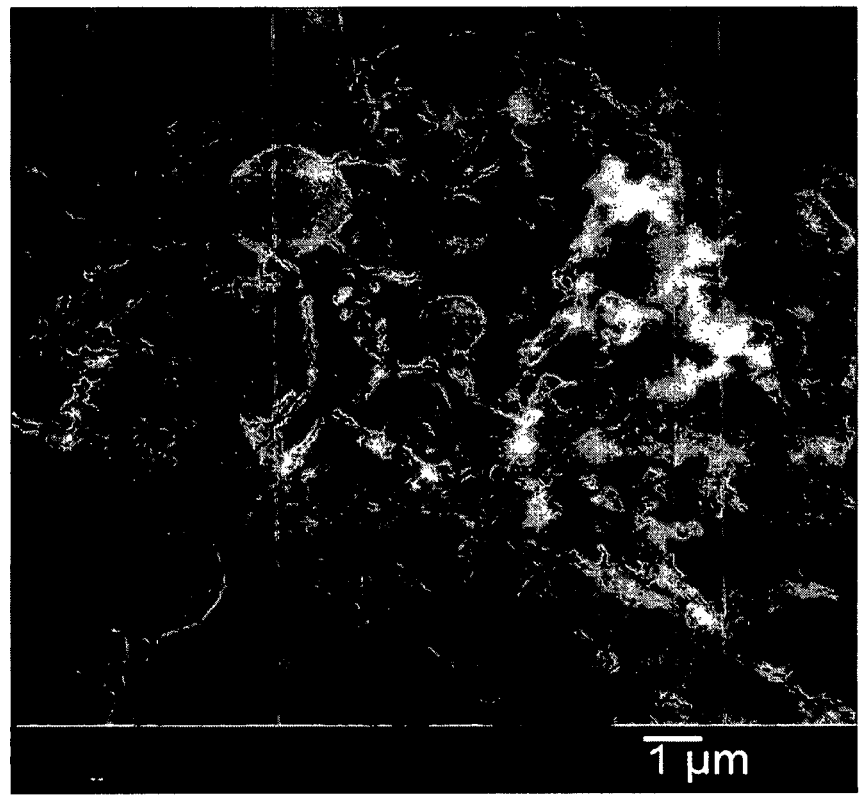

Results and Discussion Regarding the Cellular Association of Chitosan/GMO Nanoparticles The in vitro bioadhesion of the delivery system was evaluated in MDA-MB-231 human breast cancer cells (FIGS. 4A and 4B). The SEM micrographs of MDA-MB-231 cells treated in the vehicle alone show no remarkable nanoparticulate nodules when compared to monolayers treated with the chitosan/GMO nanoparticle formulation following 30 minutes of exposure (FIGS. 3A and 3B). The SEM micrograph confirmed the particle size and demonstrated the bio-adhesive properties of the chitosan/GMO formulations to the inherent negative cell surface-charge of the MDA-MB-231 cells (FIG. 4B). The chitosan/GMO particles size distribution ranged from approximately 500 nm to around 1 μm. This suggests the chitosan/GMO particles appear to be in a swollen hydrated state attached to the cellular surface. In addition, the expression of integral protein appears high in the cell surface morphology of the human MDA-MB-231 cells. Furthermore, the particle adherence also appears to have destabilized the cell surface morphology due to the charge-charge interactions of the particles with the cellular surface proteins when compared to the control cells. These data suggest that this formulation can adhere to the carbohydrates/glycoconjugate sites expressed on cancerous cells, and may have a preference for the over-expressed mucopolysaccharides on the cell surface of cancerous cells. The idea of bioadhesive properties have been of interest in the oral dosage forms of poorly absorbable drugs to adhere to the mucous membranes lining the gastrointestinal tract to increase the residence time. Studies have shown chitosan coated liposomes to have mucoadhesive properties in an in vitro intestinal rat model (Takeuchi et al., "Mucoadhesive Nanoparticulate Systems for Peptide Drug Delivery," *Adv. Drug Deliv. Rev.*, 47(1):39-54 (2001), which is hereby incorporated by reference). Additionally, Sandri and colleagues evaluated the mucoadhesion of a chitosan derivative (trimethylchitosan), and investigated the mucoadhesion of the chitosan nanosystems in vitro (Caco-2) and an ex vivo (rat jejunum) resulted in a prolonged residence time on intestinal mucosa offering a better chance for internalization (Sandri et al., "Nanoparticles Based on N-Trimethylchitosan: Evaluation of Absorption Properties Using in vitro (Caco-2 Cells) and ex vivo (Excised Rat Jejunum) Models," *Eur. J. Pharm. Biopharm,* 65 (1): 68-77 (2007), which is hereby incorporated by reference).

Figure 5:
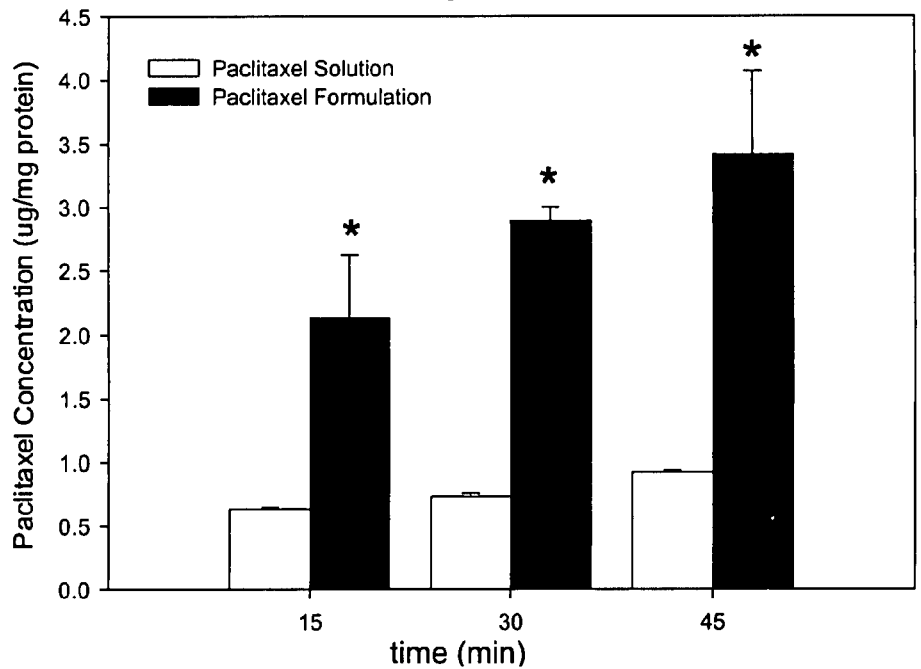
FIG. 5 is a graph showing the in vitro cellular association and uptake effects of chitosan/GMO nanoparticles loaded with PTX of the present invention. Confluent MDA-231 monolayers were exposed to paclitaxel solution (1 uM, open bars) or chitosan/GMO nanoparticles containing paclitaxel (1 uM free fraction, closed bars) at various time intervals. The data is expressed as mean±SEM of three MDA-231 monolayers and considered statistically significant when *p-value <0.05 when compared to paclitaxel alone.

The in vitro cellular association and uptake of the delivery system was further quantitatively evaluated in MDA-MB-231 human breast cancer cells (FIG. 5). The cellular association and uptake of paclitaxel was significantly increased with the nanoparticle formulation when compared to a solution of free paclitaxel throughout the entire study period. In addition, the increase in cellular association of PTX appears constant in a time dependent manner for both treatment groups. Furthermore, the increase was approximately 4 fold higher in the chitosan/GMO formulation containing paclitaxel when compared to the free form of paclitaxel throughout the entire study period. The same mucoadhesive properties of chitosan have been shown effective in the delivery of various molecules in adenocarcinomas both in vitro and in vivo (Jeong; Howard et al., "RNA Interference In vitro and In vivo Using a Novel Chitosan/siRNA Nanoparticle System, *Mol. Ther.,* 14 (4): 476-484 (2006); and Shikata et al., "In vitro Cellular Accumulation of Gadolinium Incorporated into Chitosan Nanoparticles Designed for Neutron-Capture Therapy of Cancer," *Eur. J. Pharm. Biopharm.,* 53 (1): 57-63 (2002) ("Shikata"), which are hereby incorporated by reference). Shikata and colleagues demonstrated increased cellular internalization of drug loaded chitosan nanoparticles in squamous cell carcinomas (SCC-VII) and melanoma cells (B16F10) when compared to drug solutions alone (Shikata, which is hereby incorporated by reference). In agreement with these studies, the present study also provides evidence of the mucoadhesive properties of chitosan to human breast cancer cells (MDA-MB-231) in vitro. In addition to the mucoadhesive properties, the present study also demonstrated an increased cellular association of PTX when loaded into chitosan/GMO nanoparticles to MDA-MB-231 cells in vitro. Furthermore, the increased cellular association of PTX in the nanoparticle preparations corresponded to a significant increase in cell cytotoxicity.

Example 5

The Cytotoxicity Profile of Chitosan/GMO Nanoparticles

Figure 6A:
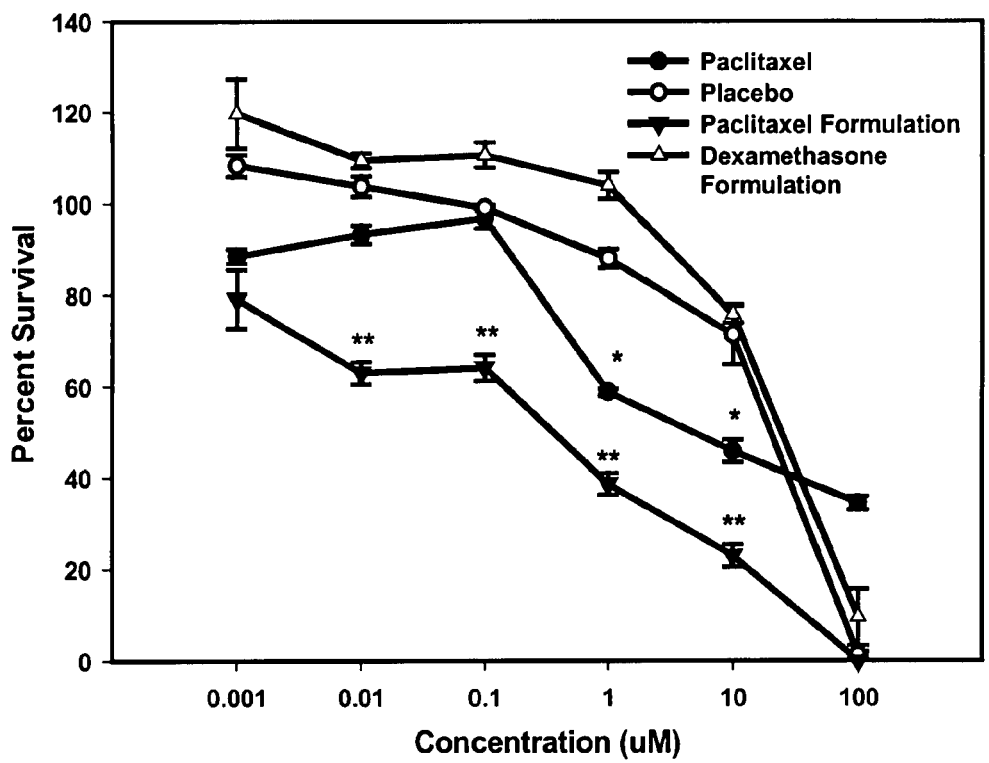
FIGS. 6A, 6B and 6C are graphs showing the in vitro cytotoxicity effects of chitosan/GMO nanoparticles at 48, 72, and 96 hours post-treatment, respectively. Confluent MDA-231 monolayers were exposed to various concentrations of PTX solution (closed circles), placebo (blank chitosan/GMO nanoparticles) (open circles), chitosan/GMO nanoparticles containing PTX (closed triangles), or chitosan/GMO nanoparticles containing DEX. The data is expressed as mean±SEM of three MDA-231 monolayers. The data was considered statistically significant when *p-value<0.05 when compared to placebo or **p-value<0.05 compared to paclitaxel solution and placebo.
Figure 6B:
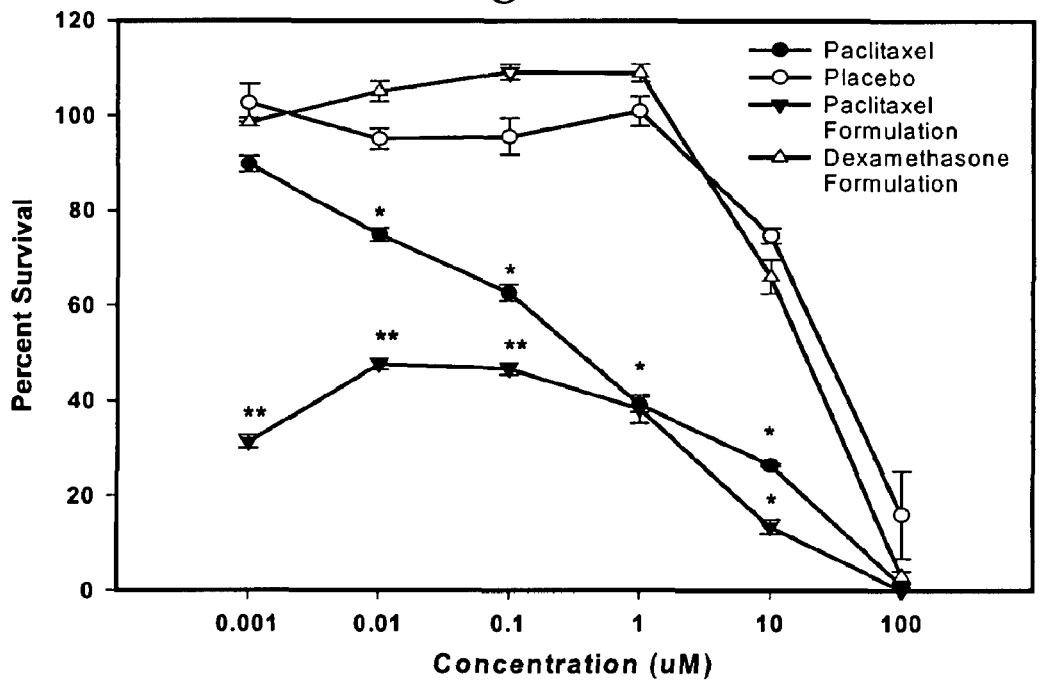
Figure 6C:
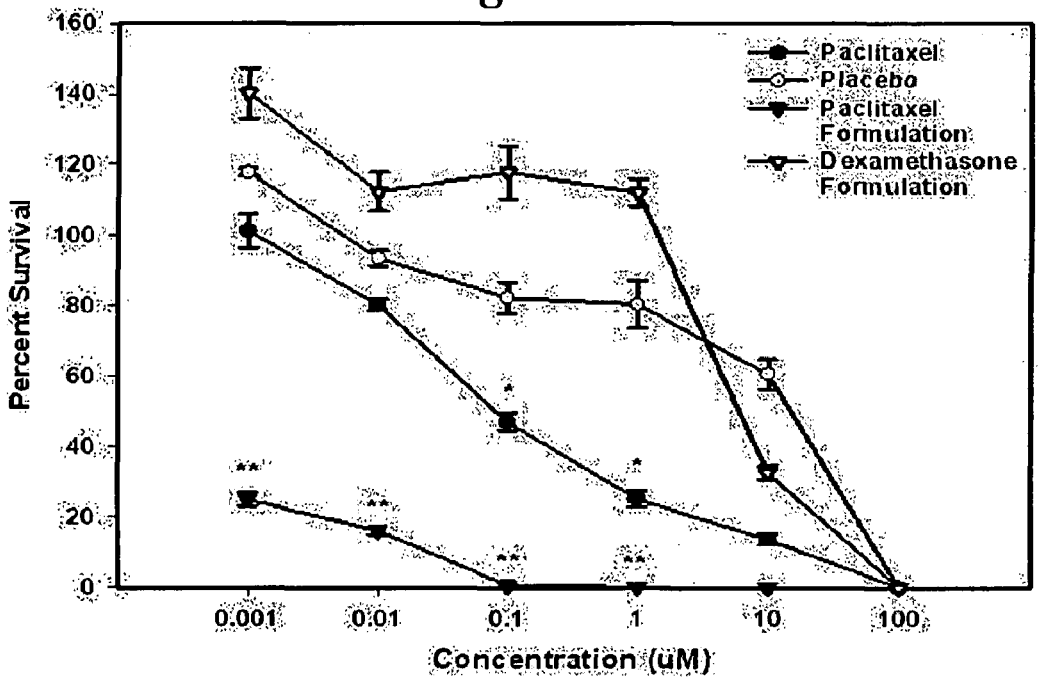

The MTT cytotoxicity dose-response studies revealed that the placebo (blank nanoparticles)≦1 mg/ml demonstrated a 100 percent cell-survival in MDA-MB-231 cells. The dose-response studies further revealed that MDA-MB-231 cells exposed to the same dose (PTX solution versus amount released PTX from the formulation) of PTX for 4 hours demonstrated a significant increase in cell death associated with the formulation when compared to PTX solution alone (FIGS. 6A, 6B, and 6C). The fold $IC_{50}$ decrease for PTX formulation was approximately 650, 500, and 1000 at 48, 72, and 96 hours post treatment when compared to the PTX solution (conventional therapy) alone (FIGS. 6A, 6B, and 6C, respectively). The significance of these data is that the bioadhesive and sustained delivery properties of the nanoparticulate formulation increases the residence or resonance time of the drug and, thus, increases the duration of chemotherapeutic effect of PTX.

In conclusion, the work experiments described in Examples 1-5 show that chitosan/GMO can form polycationic nano-sized particles with the therapeutic agent entrapped, absorbed, or chemically coupled in the bio-polymeric matrices. In addition, the formulation demonstrates high yields and entrapment efficiencies of therapeutic agents with sustained release characteristics. This formulation can be stored in a lyophilized powder that is easily re-suspended in an aqueous matrix. Again, while not intending to be bound by any mechanism by with the above pharmaceutical compositions and methods may operate, it is believed that the nanoparticles may have a hydrophobic inner-core surrounded by a hydrophilic coating which exhibits a significant positive charge suggesting that chitosan is a surface modification. Furthermore, the chitosan/GMO nanoparticles show evidence of significant mucoadhesive properties, increased cellular association, and presumably intercellular internalization in MDA-MB-231 cells. This suggests that the positive surface charge may aid in the mucoadhesive properties of the drug delivery system to adhere to the carbohydrates/glycoconjugate sites over-expressed on cancerous cells, and the formulation may have a preference for the over-expressed mucopolysaccharides on the cell surface of cancerous cells. These advantages may allow lower doses of PTX to achieve an efficacious therapeutic window, thus, minimizing the adverse side effects associated with chemotherapeutics like PTX.

Example 6

Figure 7A:
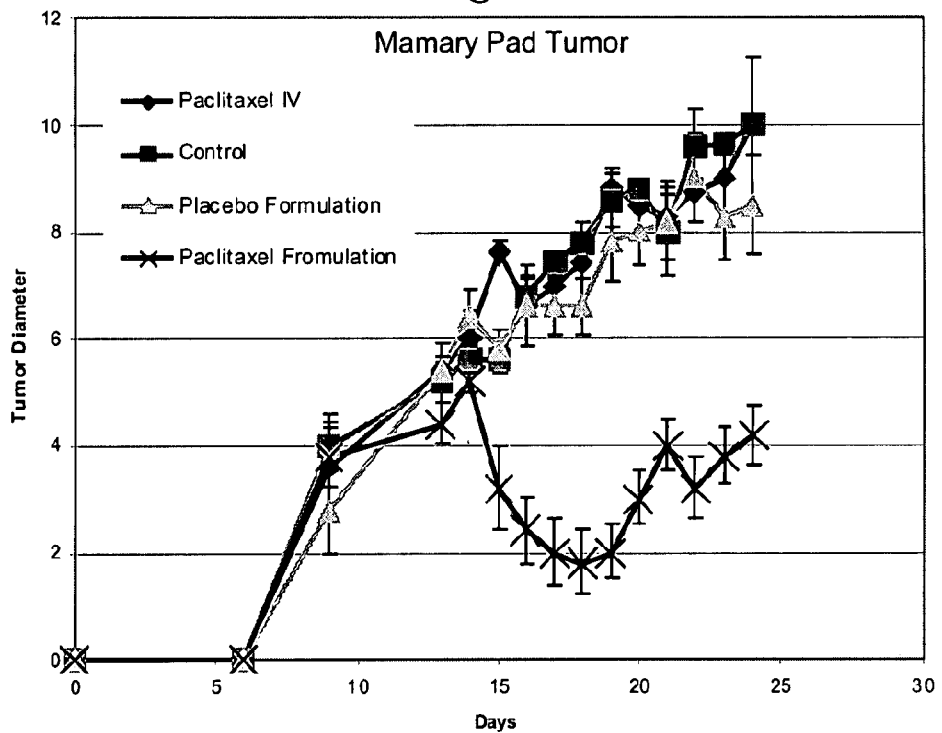
FIGS. 7A and 7B are graphs of mammary pad tumor (FIG. 7A) and flank tumor (FIG. 7B) diameter as a function of time showing the effectiveness of local delivery versus systemic administration of various chemotherapeutic formulations and controls in SCID mice. Control mice (solid squares) received no treatment; PTX IV mice (solid diamonds) received PTX solution tail vein (15 mg/kg, for 3 days); placebo group (solid triangles) received a single bolus local injection of chitosan/GMO nanoparticles without PTX (15 mg/kg formulation weight); and PTX formulation group (crosses) received a single bolus local injection of chitosan/GMO nanoparticles with PTX of the present invention (15 mg/kg formulation weight). The tumor diameter data is expressed as mean±SEM, n=6 animals.
Figure 7B:
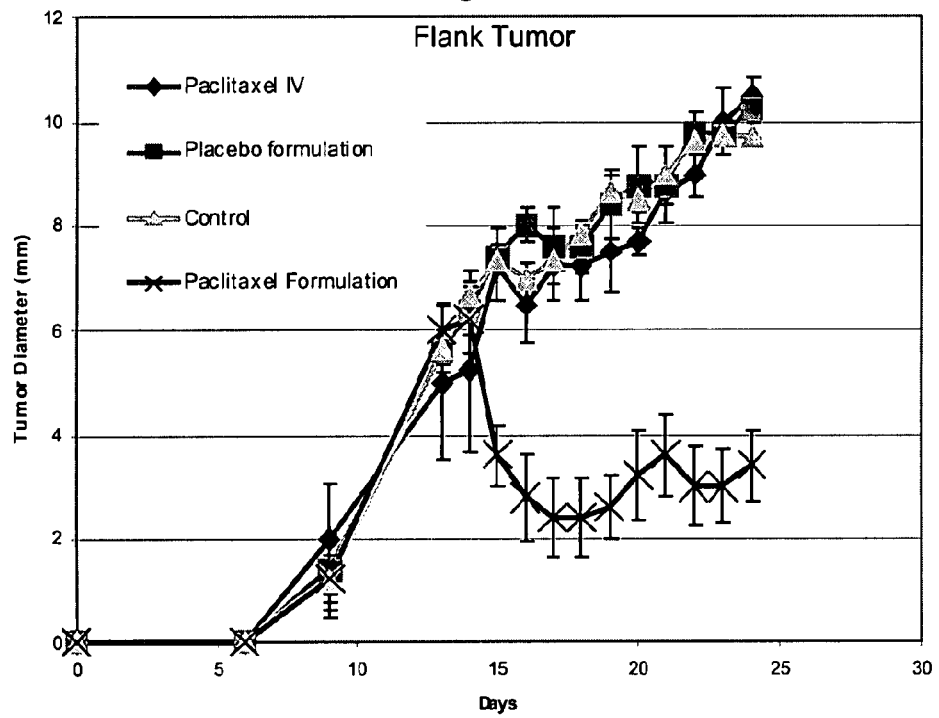

In Vivo Comparison of the Effectiveness of Local Delivery Versus Systemic Administration The safety and efficacy of the localized PTX nanoparticulate DDS was compared to the conventional route for PTX administration in an in vivo model of human breast cancer (FIGS. 7A and 7B). The rationale for using an in vivo model is to mimic the clinical situation of localized disease, i.e., carcinoma in situ and flank malignant tumor growth. Briefly, in these studies, Fox Chase SCID Female Mice with CB17 background (7 weeks old) mice were purchased from Charles Rivers Laboratories. MDA-MB-231 human breast cancer cells were cultured as described above. On the day of injections, a MDA-MB-231 were collected and resuspended (30 million cells/ml) in RPMI 1640 serum free media. The mice received an injection (0.1 ml) in the fourth inguinal mammary pad and another subcutaneous injection (0.1 ml) in the ipsilateral flank. Both the mammary pad and the flank tumor development along with the animal weight were monitored at various intervals throughout the entire study. On day 14, the mice were randomly separated into four groups for treatment as follows: control (no treatment); PTX standard clinical IV solution (15 mg/kg, tail vein, one dose each day for 3 days); placebo (blank nanoparticle formulation) (15 mg/kg, total formulation weight); PTX (4.5% w/w) nanoparticle formulation (15 mg/kg, total formulation weight). Therefore, the total PTX dose for the nanoparticle formulation was determined to be 0.625 mg/kg. The nanoparticle formulations were suspended in sterile water just prior to injection. On day 14, each animal received the respective treatment either intravenous or localized intratumoral injection in both tumors. On day 21, a second dose was administered. The data is expressed as mean±SEM, n=6.

After the initial MDA-MB-231 cell injection, tumor development was visible after 6 days and measurable on day 9 (FIGS. 7A and 7B). The tumor diameter increased at a constant rate for all the groups between day 7 and day 14 (FIGS. 7A and 7B). After a single intratumoral bolus dose of the PTX formulated nanoparticles, a significant decrease (50%) in tumor diameter in both the mammary pad and the flank was observed on day 15 when compared to control, placebo, and PTX administered intravenous (FIGS. 7A and 7B). At four days post treatment, the tumor diameter reached the maximal decrease in diameter to approximately 72% in both the mammary pad and the flank when compared to control, placebo, and PTX administered intravenous (FIGS. 7A and 7B). Even though, the tumor shrinkage reached a significant reduction in diameter by day 18 in both the mammary pad and the flank, the difference was reduced to approximately 50% by day 21 in both the mammary pad and the flank when compared to control, placebo, and PTX administered intravenous (FIGS. 7A and 7B). At this point in the study, all the groups received a second treatment on day 21 (FIGS. 7A and 7B).

Example 7

Preparation and Characterization of Gemcitabine Nanoparticle Consisting of Chitosan and Glycerol Monooleate This Example 7 describes experiments designed to develop, characterize the physiochemical properties, and evaluate the safety and efficacy of a nanoparticle drug delivery system containing chitosan/GMO and gemcitabine ("GEM") in an in vitro pancreatic cancer model. The delivery system was prepared by a multiple emulsion (o/w/o) solvent evaporation method consisting of GMO, low molecular weight chitosan, and 0.5% aqueous polyvinyl alcohol (MW 30,000-70,000). The final multiple oil-water emulsion was washed, concentrated by centrifugation, and freeze-dried. The particle size and surface charge were determined by a zeta-meter. The GEM encapsulation, in vitro release, and in vitro cellular association were evaluated by a rapid, high sensitive HPLC method (Luna 18 column (4.6×250 mm), 95/5 (v/v) 0.4 M ammonium acetate/acetonitrile mobile phase (pH 5.5), 1 ml/min flow rate, and 268 nm UV detection). Human pancreatic cancer cells (MiaPaCa-2 and BxPC-3) were purchased from ATCC and cultured accordingly. The safety and efficacy were evaluated by MTT cytotoxicity assay at various time intervals (48 to 96 hours). The chitosan/GMO blank formulation yielded a nano-sized particle (432.0±16.3 nm) and a highly positive charge (+31.78±0.54). Similar results were also observed for the 2.0% GEM and 4.0% GEM loaded formulations ((382.3+28.6, ±21.94±4.37); (385.2±16.1, ±21.23±1.46)). The in vitro release characteristics revealed an initial burst release (45%) followed by a slow terminal release (0.35% per hour). The MTT-cytotoxicity dose-response studies revealed the placebo at or below 1 mg/ml showed 100% cell survival. These dose-response studies further revealed MiaPaCa-2 and BxPC-3 cells exposed to an equal fraction (GEM solution-vs.-released GEM from the formulation) of GEM for 4 hours demonstrated a significant decrease in the $IC_{50}$ (2 log shift) in cell survival for the GEM formulation at 48, 72, and 96 hours post treatment when compared to the GEM in solution.

The study shows that drug delivery systems containing chitosan/GMO and GEM can form nanoparticles that are easily resuspended in an aqueous medium; that the nanoparticles are safe; and that the GEM loaded nanoparticles have an increased effectiveness compared to GEM treatment alone in an in vitro model of human pancreatic cancer.

Example 8

Cellular Uptake and Sub-Cellular Localization Studies

This Example 8 describes experiments designed to evaluate the cellular uptake and sub-cellular localization of nanoparticle drug delivery systems containing chitosan/GMO.

The delivery system was prepared by a multiple emulsion (o/w/o) solvent evaporation method consisting of GMO, low molecular weight chitosan, and 0.5% aqueous polyvinyl alcohol (MW 30,000-70,000). The final multiple oil-water emulsion was washed, concentrated by centrifugation, and freeze-dried. The particle size and surface charge were determined by a zeta-meter. The coumarin-6 ("CM-6") or rhodamine-123 ("R123") loading, release, and cellular uptake were evaluated by a rapid HPLC method that is highly sensitive (LOD 0.1 µg/ml), NovaPac c8 column, 70:30 (v/v) acetonitrile/1 mM 1-heptane-sulphonic acid or 1 mM 1-heptane-sulphonic acid mobile phases for CM-6 or R123, 0.2 ml/min flow rate, and EX 505, EM 535 nm fluorescent detection). Human breast, cancer cells (MDA-MB-231) were purchased from ATCC and cultured accordingly. The fluorescent nanoparticle formulations were exposed to MDA-MB-231 cells for various time intervals (15-60 min) in the presence of TEXAS-RED™ conjugated transferin and DAPI to determine the mechanism of nanoparticle internalization and sub-cellular localization by confocal microscopy ("CFM").

The chitosan/GMO blank formulation of CM-6 and R123 yielded durable nano-sized particles (436.5+4.9 nm) and (266.6+3.3 nm) having a positive surface charge (+32.1±6.15 mV) and (+30.6±0.31 mV). The percent CM-6 or R123 release was negligible (<1%) following 4 hours exposure at pH-4 or pH-7. HPLC methods revealed the cellular association of chitosan/GMO nanoparticles increased in a time-dependent manner. The CFM images further qualitatively substantiate the increased bioadhesive properties and cellular internalization of the chitosan/GMO nanoparticles. The fluorescent nanoparticles were rapidly (5 min) observed internalized in MDA-MB-231 cell monolayers. Additionally, the CFM images demonstrated both early-endosomal and lysosomal internalization mechanisms with lysosomal escape as early as 10 minutes after exposure. Furthermore, the chitosan/GMO formulation demonstrated nuclear colocalization with the DAPI fluorescent dye within 10-30 minutes of exposure.

The study shows that the chitosan/GMO formulation has increased cellular bioadhesive properties and significant cellular internalization. The chitosan/GMO nanoparticle formulation clearly colocalized in the nuclear compartment. In addition, chitosan/GMO nanoparticle formulations are suitable candidates to deliver genes of interest for various disease states including breast cancer.

Example 9

Figure 8A:
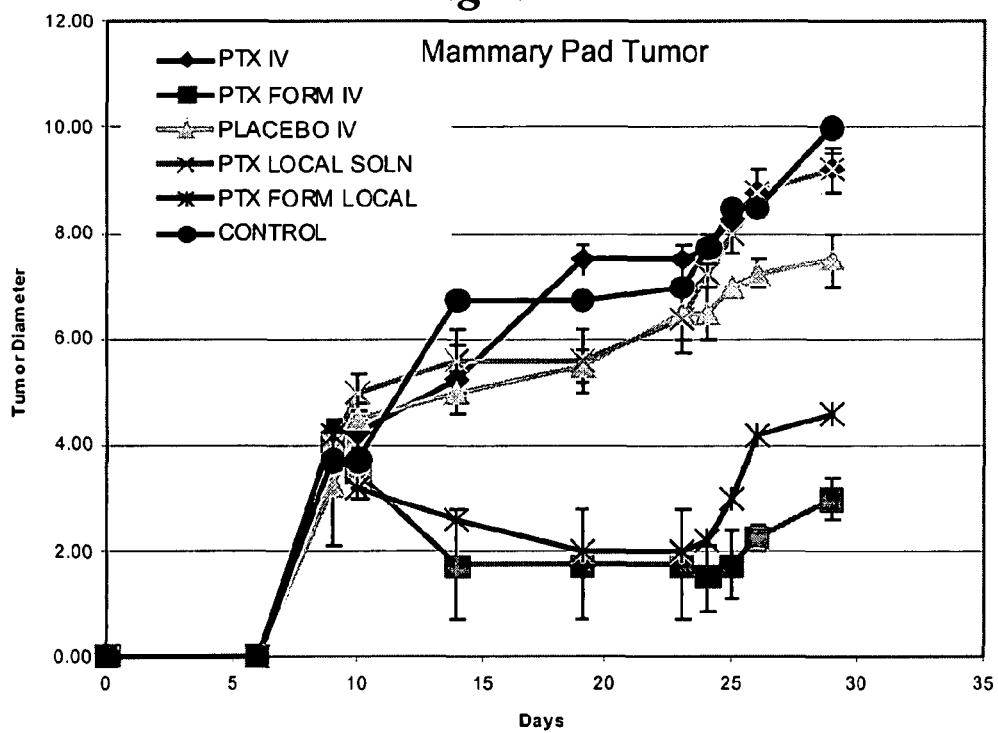
FIGS. 8A and 8B are graphs of mammary pad tumor (FIG. 8A) and flank tumor (FIG. 8B) diameter as a function of time showing the effectiveness of localized PTX formulated in chitosan/GMO nanoparticles as compared to systemic administration in SCID mice. Control mice received no treatment, PTX IV mice received PTX solution tail vein (15 mg/kg, for 3 days), PTX Local Solution (0.625 mg/kg), Placebo group received a tail vein injection of chitosan/GMO nanoparticles without PTX (15 mg/kg formulation weight), and PTX formulation IV group received a tail vein injection of chitosan/GMO nanoparticles with PTX (15 mg/kg formulation weight), and PTX Formulation local received a single bolus local injection of chitosan/GMO nanoparticles with PTX (15 mg/kg formulation weight). The tumor diameter data is expressed as mean±SEM, n=6 animals.
Figure 8B:
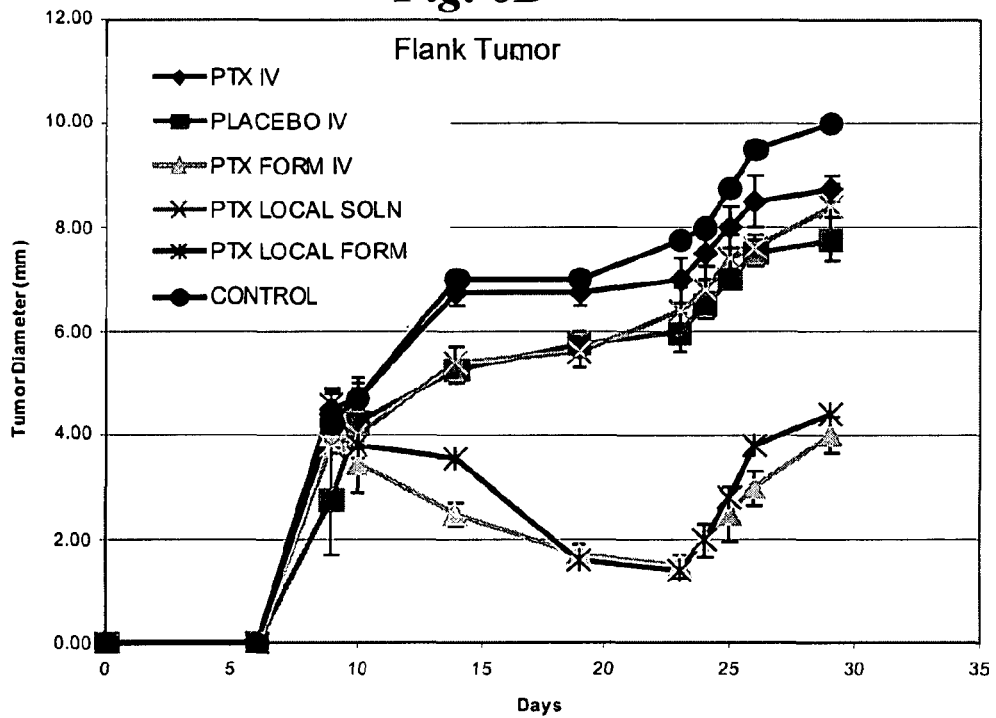

In Vivo Comparison of the Effectiveness of Local Delivery Versus Systemic Administration The safety and efficacy of the localized PTX nanoparticulate DDS was compared to the conventional route for PTX administration in an in vivo model of human breast cancer (FIGS. 8A and 8B). The rationale for using an in vivo model is to mimic the clinical situation of localized disease, i.e., carcinoma in situ and frank malignant tumor growth. Briefly, in these studies, Fox Chase SCID Female Mice with CB17 background (7 weeks old) mice were purchased from Charles Rivers Laboratories. MDA-MB-231 human breast cancer cells were cultured as described above. On the day of injections, MDA-MB-231 were collected and resuspended (30 million cells/ml) in RPMI 1640 serum free media. The mice received an injection (0.1 ml) in the fourth inguinal mammary pad and another subcutaneous injection (0.1 ml) in the ipsilateral flank. Both the mammary pad and the flank tumor development along with the animal weight were monitored at various intervals throughout the entire study. On day 9, the mice were randomly separated into six groups for treatment as follows: control (no treatment), PTX standard clinical IV solution (15 mg/kg) tail vein, one dose each day for 3 days in one group or 0.625 mg/kg administered locally in another group, placebo (blank nanoparticle formulation) (15 mg/kg, total formulation weight) tail vein, one dose each day for 3 days; PTX (4.5% w/w) nanoparticle formulation (15 mg/kg, total formulation weight) administered as either a single bolus dose locally in one group or 15 mg/kg, total formulation weight) tail vein in another group, one dose each day for 3 days. Therefore, the total PTX dose for the nanoparticle formulation was determined to be 0.625 mg/kg. The nanoparticle formulations were suspended in sterile water just prior to injection. On day 9, each animal received the respective treatment either intravenous or localized intratumoral injection in both tumors. The data are expressed as mean±SEM, n=6.

After the initial MDA-MB-231 cell injection, tumor development was visible after 7 days and measurable on day 9 (FIGS. 8A and 8B). The tumor diameter increased at a constant rate for all the groups between day 6 and day 9 (FIGS. 8A and 8B). After a single intratumoral bolus dose or intravenously administered PTX formulated nanoparticles, a significant decrease (65%) in tumor diameter in both the mammary pad and the flank was observed on day 14 when compared to control, placebo and PTX administered intravenous or a single intratumoral bolus (FIGS. 8A and 8B). At fourteen days post treatment, the tumor diameter reached the maximal decrease in diameter to approximately 71% in both the mammary pad and the flank when compared to control, placebo and PTX administered intravenous or a single intratumoral bolus (FIGS. 8A and 8B). Even though the tumor shrinkage reached and maintained a significant reduction in diameter until day 24 in both the mammary pad and the flank, the difference was reduced to approximately 50% by day 28 in both the mammary pad and the flank when compared to control, placebo and PTX administered intravenous or a single intratumoral bolus (FIGS. 8A and 8B).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for treating a cancer in a subject comprising the steps of:
   providing a pharmaceutical composition for delivery to a cancer cell, wherein the pharmaceutical composition comprises a plurality of nanoparticles, wherein each nanoparticle of the plurality of nanoparticles is formed comprising the steps of:
      supplying a glyceryl monooleate fatty acid ester core and surface layer,
      placing a chitosan on the surface layer of the glyceryl monooleate fatty acid ester to create a positively charged surface layer in order to make each nanoparticle more mucoadhesive to negatively charged mucin of the cancer cell, and
      incorporating a cancer therapeutic agent into the core of the glyceryl monooleate fatty acid ester; and
   administering the pharmaceutical composition to the subject.

2. The method according to claim 1, wherein said administering step further comprises the step of supplying the composition parenterally.

3. The method according to claim 2, wherein said supplying step further comprises the step of injecting the composition close to the site of a tumor.

4. The method according to claim 1, wherein said administering step further comprises the step of supplying the composition intravenously.

5. The method according to claim 1, wherein the cancer is one in which transmembrane mucin glycoproteins are overexpressed.

6. The method according to claim 1, wherein the cancer is breast cancer.

7. The method according to claim 1, wherein the cancer is pancreatic cancer.

8. The method according to claim 1, wherein the cancer is colon cancer.

9. The method according to claim 1, wherein the subject is a human.

10. The method according to claim 1, wherein the glyceryl mono fatty acid ester is oleyl glycerate.

11. The method according to claim 1, wherein the plurality of nanoparticles further comprises a D-alpha-tocopheryl polyethylene glycol 1000 succinate.

12. The method according to claim 1, wherein the cancer therapeutic agent is paclitaxel.

13. The method according to claim 1, wherein the cancer therapeutic agent is gemcitabine.

14. The method according to claim 1, wherein said administering step further comprises the step of supplying the composition orally.

* * * * *